US007416893B2

(12) United States Patent
DeBernardi et al.

(10) Patent No.: US 7,416,893 B2
(45) Date of Patent: Aug. 26, 2008

(54) METHODS FOR DIAGNOSING DRUG-RESISTANT CANCER CELLS OR FOR IDENTIFYING CHEMOTHERAPEUTIC AGENTS BY MEASURING ANOMALOUS INTRACELLULAR ION AND/OR SECOND MESSENGER DYNAMICS

(75) Inventors: Maria A. DeBernardi, Potomac, MD (US); Gary Brooker, Rockville, MD (US)

(73) Assignee: Atto Bioscience, Rockville, MD (US)

( * ) Notice: Subject to any disclaimer, the term of this patent is extended or adjusted under 35 U.S.C. 154(b) by 425 days.

(21) Appl. No.: 10/313,039

(22) Filed: Dec. 6, 2002

(65) Prior Publication Data

US 2004/0110244 A1 Jun. 10, 2004

(51) Int. Cl.
G01N 33/48 (2006.01)
G01N 33/483 (2006.01)
(52) U.S. Cl. .............................. 436/34; 436/64; 436/79
(58) Field of Classification Search ........................ None
See application file for complete search history.

(56) References Cited

U.S. PATENT DOCUMENTS

| 5,332,905 | A | * | 7/1994 | Brooker et al. ........... 250/458.1 |
| 5,677,288 | A | * | 10/1997 | Marangos ..................... 514/39 |
| 5,858,713 | A | * | 1/1999 | Soderlund et al. .......... 435/69.1 |
| 6,171,786 | B1 | * | 1/2001 | Shtil et al. ...................... 435/6 |
| 6,420,137 | B1 | * | 7/2002 | Strnad et al. ............... 435/69.1 |

FOREIGN PATENT DOCUMENTS

WO     WO 99/28747     *   6/1999

OTHER PUBLICATIONS

Nickols and Brooker (PNAS, 1978, vol. 75, pp. 5520-5524).*
Henderson et al (Journal of Biological chemistry, 1991, vol. 266, pp. 1641-1645).*
abstract of Hoyal et al (Journal of Toxicology and Environmental Health, Part B, 1998, vol. 1, pp. 117-134).*
abstract of Mousseau et al (European Journal of Cancer, 1993, vol. 29A, pp. 753-759).*
DeBernardi and Brooker (Methods in Enzymology, 2006, vol. 414, pp. 317-335).*
abstract of MacLeod (Cardioscience, 1991, vol. 2, pp. 71-85).*
Adwankar et al., "Modulation of in vitro chemosensitivity by extracellular $Ca^{++}$ in adriamycin sensitive and resistant P388 leukemic cells," *Neoplasma* 37:31-36 (1990).
Altan et al., "Defective Acidification in Human Breast Tumor Cells and Implications for Chemotherapy," *J. Exp. Med.* 187:1583-1598 (1998).
Barrand et al., "Multidrug Resistance-Associated Protein: A Protein Distinct from P-glycoprotein Involved in Cytotoxic Drug Expulsion," *Gen. Pharmacol.* 28:639-645 (1997).
Blobe et al., "Selective Regulation of Expression of Protein Kinase C (PKC) Isoenzymes in Multidrug-resistant MCF-7 Cells," *J. Biol. Chem.* 268:658-664 (1993).
Chen et al., "Identification of Glutathione S-Transferase as a Determinant of 4-Hydroperoxycyclophosphamide Resistance in Human Breast Cancer Cells," *Biochem. Pharmacol.* 49:1691-701 (1995).
Dickstein et al., "Increased Epidermal Growth Factor Receptor in an Estrogen-Responsive, Adriamycin-Resistant MCF-7 Cell Line," *J. Cell. Physiol.* 157:110-118 (1993).
Doyle et al., "A multidrug resistance transporter from human MCF-7 breast cancer cells," *Proc. Natl. Acad. Sci. USA* 26:15665-15670 (1998).
Lavie et al., "Agents that Reverse Multidrug Resistance, Tamoxifen, Verapamil, and Cyclosporin A, Block Glycosphingolipid Metabolism by Inhibiting Ceramide Glycosylation in Human Cancer Cells," *J. Biol. Chem.* 272:1682-1687 (1997).
McAlroy et al., "Drug Extrusion, $^{125}I^-$Efflux and the Control of Intracellular $[Ca^{2+}]$ in Drug-Resistant Ovarian Epithelial Cells," *Exp. Physiol.* 84:285-897 (1999).
Mestdagh et al., "Comparative Study of Intracellular Calcium and Adenosine 3',5'-Cyclic Monophosphate Levels in Human Breast Carcinoma Cells Sensitive or Resistant to Adriamycin®: Contribution to Reversion of Chemoresistance," *Biochem. Pharmacol.* 48:709-716 (1994).
Morgan et al., "Multidrug resistance in MCF-7 human breast cancer cells is associated with increased expression of nucleoside transporters and altered uptake of adenosine," *Canc. Chemother. Pharmacol.* 29:127-132 (1991).
Ogretmen et al., "Down-Regulation of Apoptosis-Related bcl-2 but not $bcl-x_L$ or bax Proteins in Multidrug-Resistant MCF-7/Adr Human Breast Cancer Cells," *Int. J. Cancer* 67:608-614 (1996).
Rubin, "The significance of biological heterogeneity," *Cancer and Metastasis Reviews* 9:1-20 (1990).
Schneider et al., "Multidrug Resistance-associated Protein Gene Overexpression and Reduced Drug Sensitivity of Topoisomerase II in a Human Breast Carcinoma MCF7 Cell Line Selected for Etoposide Resistance," *Cancer Res.* 54:152-158 (1994).

(Continued)

*Primary Examiner*—Karen A. Canella
(74) *Attorney, Agent, or Firm*—Cooley Godward Kronish LLP

(57) ABSTRACT

The present invention relates to methods of identifying drug-resistant and/or drug-sensitive cells, for example, breast cancer and brain tumor cells, on the basis of different ion and/or second messenger dynamics between a drug-sensitive and drug-resistant cell. For example, the invention provides measuring the comparative decay rates of a cellular ion, such as calcium, released into the intracellular compartment of drug sensitive and/or drug resistant cells. The present invention also provides methods for screening compounds that modulate the ionic dynamics of a cell as well as methods of determining drug resistance/sensitivity of cancer cells from cancer patients and/or designing cancer therapy based on of the ionic dynamics of cancer cells from a particular patient.

25 Claims, 7 Drawing Sheets

OTHER PUBLICATIONS

Sinha et al., "Differential Formation of Hydroxyl Radicals by Adriamycin in Sensitive and Resistant MCF-7 Human Breast Tumor Cells: Implications for the Mechanism of Action," *Biochemistry* 26:3776-3781 (1987).

Wolffe et al., "Primary culture, cellular stress and differentiated function," *FEBS Letters* 176:8-15 (1984).

Wosikowski et al., "Altered Gene Expression in Drug-resistant Human Breast Cancer Cells," *Clin. Cancer Res.* 3:2405-14 (1997).

* cited by examiner

METHODS FOR DIAGNOSING DRUG-RESISTANT CANCER CELLS OR FOR IDENTIFYING CHEMOTHERAPEUTIC AGENTS BY MEASURING ANOMALOUS INTRACELLULAR ION AND/OR SECOND MESSENGER DYNAMICS

STATEMENT REGARDING FEDERALLY FUNDED PROJECT

The United States Government owns rights in the present invention pursuant to RO1 HL 28940 from the National Institutes of Health.

BACKGROUND OF THE INVENTION

1. Field of the Invention

The present invention relates to methods of identifying drug-resistant and/or drug-sensitive cells, for example, breast cancer and brain tumor cells, on the basis of different ion and/or second messenger dynamics between a drug-sensitive and drug-resistant cell. For example, the invention provides measuring the comparative decay rates of a cellular ion, such as calcium, released into the intracellular compartment of drug sensitive and/or drug resistant cells. The present invention also provides methods for screening compounds that modulate the ionic, dynamics of a cell as well as methods of determining drug resistance/sensitivity of cancer cells from cancer patients and/or designing cancer therapy based on of the ionic dynamics of cancer cells from a particular patient.

2. Discussion of the Background

The emergence of drug-resistant cancer cells represents a major therapeutic problem. When a cancer develops drug resistance, treatment protocols must be modified, for example, by administering a higher drug dose or switching the patient to a different drug combination or regimen.

Cancer cells that are exposed to a cytotoxic agent for a prolonged period of time often become resistant to that agent, as well as other chemically unrelated compounds. This resistance represents a major cause for chemotherapy failure in cancer patients, such as breast cancer patients. Moreover, some cancers, such as breast cancer, may develop resistance to multiple drugs further aggravating the problem. Such drug-resistances may be attributed to both phenotypic and genotypic changes in a drug-resistant cancer cell. For example, the expression or upregulation of P-glycoprotein (P-gp, permeability glycoprotein) or other multidrug resistance genes, can alter the absorption, distribution, or clearance of a variety of compounds. Drug-resistant human cancer cells are well known and can be produced by exposing a drug-sensitive parental cell line to a drug, and then selecting drug resistant variants of the parental cell line. Such cells are valuable research tools for studying the mechanisms associated with the development of drug resistance. In vitro, drug-resistant (DR) cells and drug-sensitive (DS) cells exhibit a variety of different biochemical features. For example, compared to drug-sensitive breast cancer cells, drug resistant breast cancer cells may exhibit one or more of the following biochemical features or phenotypes: over-expression of ATP-driven membrane drug efflux pumps, such as P-gp, MRP (Barrand, M. A. et al., *Gen. Pharmacol.* 28:639-45, 1997) and BCRP (Doyle, L. A. et al., *Proc. Natl. Acad. Sci., U.S.A.*, 26:15665-70, 1998); over-expression of nucleoside transporters; reduced susceptibility to oxygen radicals; increased accumulation of glycolipids; resistance to apoptosis or programmed cell death; highly acidified organelles and elevated cytosolic pH; increased protein kinase Cα content; lower basal cyclic AMP levels; or alterations in enzyme activity or gene expression (Barrand et al *Gen Pharmacol*. 28: 63945, 1997; Doyle et al *Proc. Natl. Acad. Sci*. 26.-15665-15670, 1998; Morgan et al *Cancer Chemother Pharmacol* 29: 127-32, 1991; Sinha et al *Biochemistry* 26:3776-81, 1987; Lavie et al *J Biol Chem* 272: 1682-7, 1997; Ogretmen et al *Int J Cancer* 67:608-14, 1996; Altan et al *J Exp Med* 187:1583-98, 1998; Blobe et al *J Biol Chem*. 268:658-64, 1993; Mestdagh et al *Biochem Phannacol* 48:709-16, 1994; Chen et al *Biochem Pharmacol*. 49:1691-701, 1995; Wosikowski et al *Clin Cancer Res*. 3:2405-14, 1997; Schneider et al *Cancer Res* 54:152-8, 1994).

However, standard methods for determining whether a cancer cell has acquired drug resistance are time-consuming, lack specificity and sensitivity, require the processing of large numbers of cells, and result in the destruction of the tested cells. These methods conventionally involve exposing cells cultured in vitro to progressively increasing concentrations of a drug. Drug-resistant cells are then identified by the ability to survive or proliferate in a particular concentration of drug. However, these assays generally require the processing of large cell populations to establish drug resistance, which is measured by parameters such as $IC_{50}$, the dose of the drug that kills 50% of the cell population. Additionally, the cells must be exposed to the drug for a period of 24 to 48 hours and in some assays greater than 48 hours.

Moreover, the results of such methods may lack specificity as a cultured cell may be phenotypically or genotypically altered by prolonged exposure to an in vitro culture medium (Rubin (1990) *Cancer and Metastasis Reviews* 9:1-20; Wolffe and Tata (1984) *FEBS Letters* 176(1):8-15). Moreover, the relative percentages of drug-sensitive and drug-resistant cells are difficult to determine when cells are cultured in vitro, due to different proliferation rates of drug sensitive and drug resistant cells. Similarly, when a culture contains cancer cells with different degrees of drug resistance or different proliferative abilities, conventional methods may lead to a loss of that fraction of the culture, which is of particular importance. For example, while conventional methods would yield an $IC_{50}$ value for an entire population of cultured cells, they would not necessarily discriminate between the fraction of a cell population that represents rapidly growing drug resistant cells, and the rest of the population that may be slower growing, all of which are less drug resistant and/or drug sensitive cells.

The constraints imposed by the standard methods emphasize the need for faster, more specific, and sensitive assays that can be performed with fewer cells, preferentially at the single cell level, and which permit facile recovery of the tested cells for further expansion or testing.

The role of ion dynamics for distinguishing between drug resistant and drug-sensitive cells has not been previously investigated. For example, calcium is one of the most ubiquitous second messengers involved in a wide variety of cellular responses. The maintenance of physiological calcium levels within a cell, as well as the functional elevation of calcium levels, are highly regulated processes. Consequently, either an impaired or an excessive response of a cell to a calcium-evoking signal may negatively impact cell survival.

Thus, prior efforts have focused on the development of new drugs that might modulate cellular calcium dynamics; for example, by promoting an intracellular increase of calcium, when the cell itself is impaired in its ability to respond to calcium-elevating stimuli; restoring calcium homeostasis, when the cell is unable to reduce sustained intracellular calcium increase upon stimulation; or by inhibiting calcium increase, when a calcium response is undesirable, such as in pathophysiological states.

However, very little is known about the potential role played by cellular ions, and in particular, calcium ions, in the development of drug resistance in cancer cells. One report shows that in the adriamycin-resistant MCF-7 cell line of human breast cancer, resting $Ca^{2+}_i$ levels are higher than in parental, drug-sensitive cells and that resting $Ca^{2+}_i$ levels were reduced by verapamil, a calcium channel blocker and P-gp modulator (Mestdagh, N. et al. *Biochem. Pharmacol.* 48:709-716 (1994)). Adriamycin-resistant MCF-7 cells also are known to overexpress the epidermal growth factor (EGF) receptor, whose activation leads to increased intracellular calcium levels ($[Ca^{2+}]_i$). The reversion of such cells to drug-sensitivity correlated with the return of EGF levels to the levels exhibited by the drug-sensitive parental MCF-7 cells (Dickstein, B. et al. *J Cell Physiol* 157:110-118, (1993)). In leukemia cells, calcium levels have been reported to modulate cell sensitivity to drugs (Adwankar, M K & Chitnis, M P *Neoplasma* 37:31-36, (1990)); and in ovarian cancer cells, differences in calcium handling have also been reported between DS and DR cells (McAlroy, H. L. et al. *Exp. Physiol.* 84:285-97, (1999)).

Empirically, it has been found that compounds that independently modulate $Ca^{2+}_i$ dynamics can reverse drug resistance or chemosensitize a number of different cancers. For example, verapamil, a blocker of voltage-operated $Ca^{2+}$ channels, and cyclosporin A, an inhibitor of calcineurin, which is a $Ca^{2+}$/calmodulin-dependent protein phosphatase, are among the most widely studied chemosensitizers for tumors overexpressing P-gp.

Similarly, chemical modulators of MRP (multidrug resistance-associated protein), such as probenecid and genistein, are known. Probenecid is an organic anion transport blocker and can either depress or increase $Ca^{2+}_i$ responses in different cell systems at the concentrations used for chemosensitization. Genistein is a protein tyrosine kinase inhibitor and can prevent capacitative $Ca^{2+}$ entry upon agonist-evoked $Ca^{2+}_i$ release. However, the importance of cellular ionic dynamics, such as calcium levels, calcium flux, and/or intracellular calcium kinetics for distinguishing drug-resistant and drug-sensitive cancer cells has not been previously described.

In view of the high morbidity and mortality associated with the development of drug-resistance in cancer cells, there is a pronounced need to develop rapid methods for diagnosing the presence, type and frequency of drug-resistant cancer cells, as well as diagnosing and appropriately treating subjects having drug resistant cancer. Moreover, new methods are needed for screening compounds that modulate or reverse drug-resistance in such cells.

SUMMARY OF THE INVENTION

The present inventors have found that drug-sensitive and drug-resistant cancer cells can be distinguished based on differences exhibited in their cellular ionic dynamics, such as their intracellular calcium decay patterns. For example, drug-resistant breast or brain cancer cells exhibit altered intracellular calcium decay patterns that distinguish them from drug-sensitive parental cells.

One object of the invention is to provide a method for detecting drug-resistance, or the relative level of drug resistance, in a cell by determining its ionic dynamic compared to a control cell. For example, such a method may compare the intracellular calcium decay pattern of a cell to be tested with the intracellular calcium decay pattern of a corresponding drug-sensitive cell, or known decay patterns for similar drug sensitive or drug resistant cells.

The ionic dynamics of a cell may also be compared using parameters other than intracellular calcium decay patterns, such as by comparison of ionic redistribution, compartmentalization, response to particular agonists or inhibitors, or of ionic flux between or among different intracellular or extracellular compartments. Such measurements may be made between a cell to be tested and one or more appropriately matched control cell(s), or may be made by comparison of data obtained from a test cell with standardized, stored or archived data previously obtained from comparative control cell(s).

Another object of the invention is to provide a method for determining whether a cancer population is acquiring drug resistance, or alternatively, whether such a cancer cell population is losing resistance to a particular drug. That is, the method may be applied to determining the degree or level of drug resistance of a particular cancer cell or cancer cell population. Such a method permits the selection of an appropriate drug or chemotherapeutic agent for cancer treatment or allows the dose of such a drug or agent to be appropriately adjusted. This method may involve the longitudinal comparison of the ionic dynamics, for example, calcium dynamics of cancer cell samples obtained from a patient. Alternatively, it may be applied in vitro to cancer cells cultured in the presence of particular drugs or chemotherapeutic agents. Such an in vitro method facilitates the prediction of possible trends in acquisition or loss of drug resistance, as cells may be exposed to high concentrations of drugs, chemotherapeutic agents or agents, such as chemical, biochemical, endocrinological or immunological modulators, not suitable for use in a cancer patient.

The comparison of ionic dynamics in such a method may be based, for example, on the degree of anomaly in the ionic decay patterns exhibited by a test cell compared to cells that are more resistant or less resistant to a particular drug. Similarly, the invention provides a method for determining the rate at which a drug-sensitive cell line acquires, or a drug resistant cell line loses, resistance to a chemotherapeutic drug by measuring the development (or loss) of anomalous ionic decay patterns. For example, cells that have never been treated with a drug can be continuously exposed to a chemotherapeutic agent for a predetermined period of time and tested for the appearance of anomalous ionic dynamics and drug resistance. These tests at least provide diagnostic tools for determining the chemotherapeutic efficacy of a drug in vitro.

Another object of the invention is a method for identifying a compound or agent that modulates the ionic dynamics of a cell, e.g., calcium dynamics, by contacting a drug-sensitive or drug-resistant cell, or both, with the compound or agent to be tested and determining the ionic dynamics in the presence and absence of the tested compound or agent. Similarly, it is another object of the invention to identify, design or provide such compounds, agents or compositions that modify these cellular ionic dynamics. For example, agents that normalize intracellular calcium decay patterns could resensitize a cancer cell to drug treatment. Therefore, a method for determining which agents or drugs normalize ionic dynamics patterns would be advantageous for selecting novel agents that resensitize drug-resistant cancer to chemotherapeutic drugs.

Methods for selecting a chemotherapeutic drug that acts via a mechanism not involving the alteration of a particular ionic dynamic are also contemplated. For example, those chemotherapeutic drugs that act via a mechanism not involving the alteration of calcium dynamics. Such methods will help identify drugs that act via mechanisms not involving the alteration of calcium dynamics, such as important new classes of chemotherapeutic agents that avoid known modes of cellular drug resistance.

Methods for screening chemosensitizers that restore drug-sensitivity to an otherwise drug-resistant cell line, based on the effect of a putative chemosensitizer to renormalize ionic patterns in a drug resistant cancer cell is yet another object of the invention. Such methods provide novel compounds, such as chemical derivatives of known chemosensitizers that normalize ionic dynamics in cancer cells and resensitize cancer cells to drug treatment.

The present invention also provides rapid, specific and nondestructive methods for identifying drug resistant or drug sensitive cells. Unlike conventional methods, ionic measurements are faster (minutes), a smaller number of cells is required (single cell behavior may be monitored), and nondestructive (cells labeled with ion-sensitive fluorescent dyes, for example, could be recovered and allowed to grow). Nondestructive methods are of crucial importance when drug resistant cells need to be identified, isolated, and expanded for further biochemical or genetic studies.

Other objects of the invention include, but are not limited to, kits comprising cells and reagents for determining intracellular ions, for example, $[Ca^{2+}]_1$, decay kinetics or for screening compounds or agents, such as chemosensitizers, that reverse cellular drug-resistance, as well as software products, biochips or software-based methods for identifying drug-sensitive or drug-resistant cells.

DETAILED DESCRIPTION OF THE INVENTION

Figure 1A:
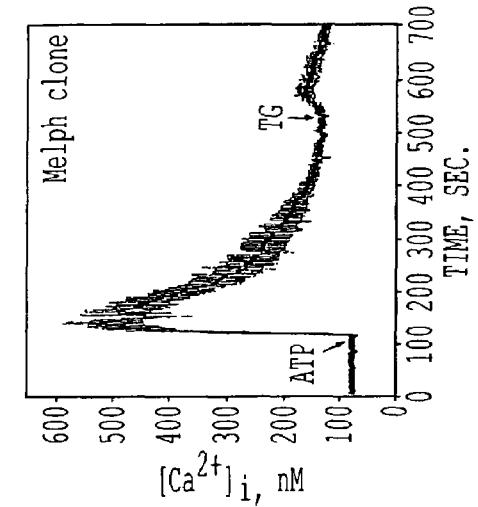
FIGS. 1(a), (b), (c), (d), (e) and (f) show the $[Ca^{2+}]_1$ increase induced in parental wild type (wt), drug sensitive (DS) and drug resistant (DR) MCF-7 cells by ATP and, subsequently, by TG (thapsigargin). The temporal profiles of $[Ca^{2+}]_1$ traces show a longer decay (meaning that $[Ca^{2+}]_1$ takes longer to return to basal level) in drug-resistant than in drug-sensitive MCF-7 cells. Also, in wild-type (drug-sensitive) and VP cells, TG does not induce $[Ca^{2+}]_1$ increase (a, b) when applied after ATP, while it does so in four different drug-resistant clones (c,d,e,f).
Figure 1B:
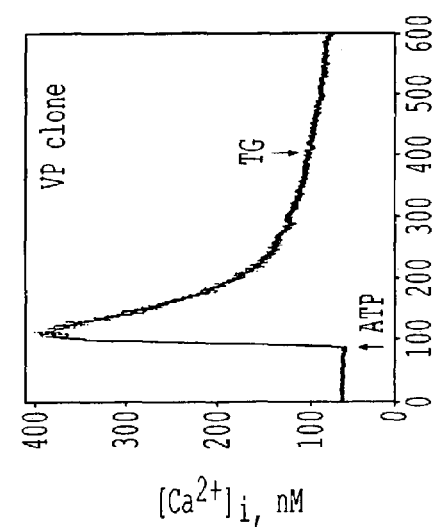
Figure 1C:
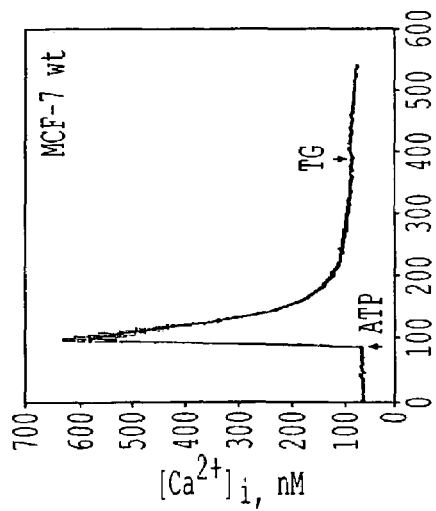
Figure 1D:
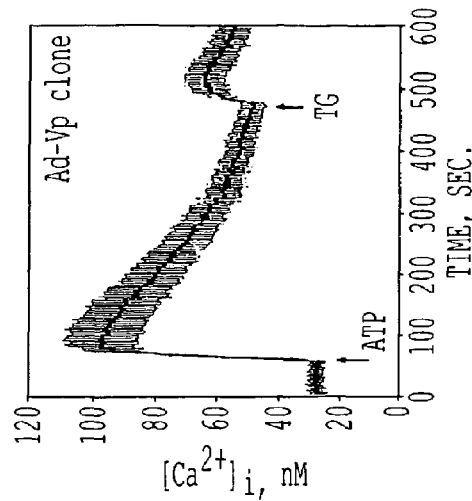
Figure 1E:
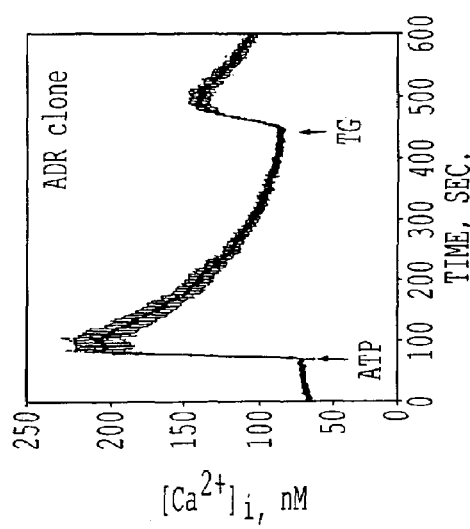
Figure 1F:
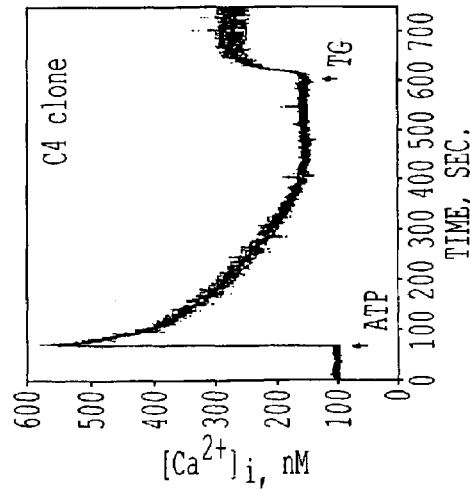
Figure 2A:
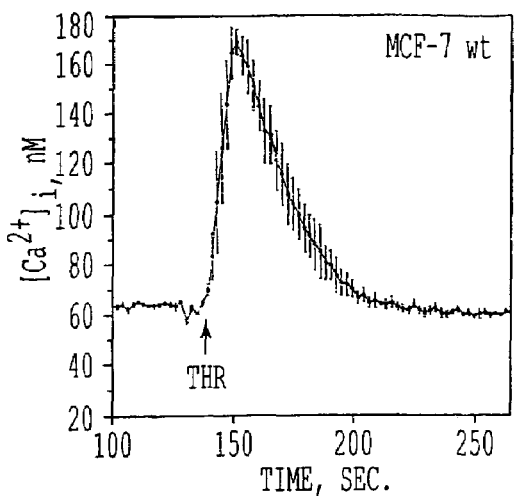
FIGS. 2(a), (b), (c), (e) and (f) show $[Ca^{2+}]_1$ responses evoked by various PI-coupled receptor agonists (THR (α-thrombin), BK (bradykinin), ATP, UTP) and TG. Intracellular calcium decay is longer in two lines of drug-resistant breast cancer cells (panels b and d) than in their corresponding drug-sensitive parental cell lines (panels a and c). Panels e and f show that MDA-MB-231 wild type cells, which are human breast cancer (estrogen receptor negative) cells never treated with drugs, exhibit fast calcium decay kinetics as seen in MCF wild type cells.
Figure 2B:
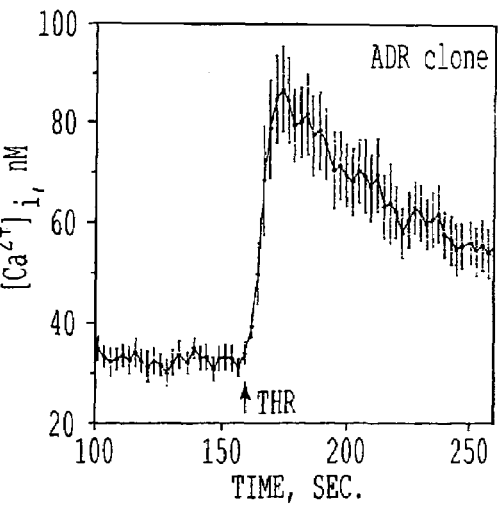
Figure 2C:
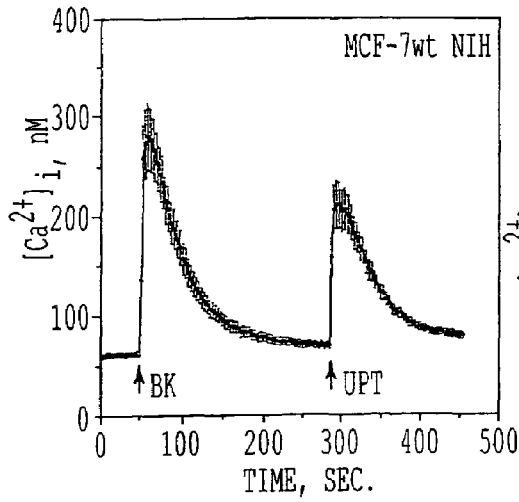
Figure 2D:
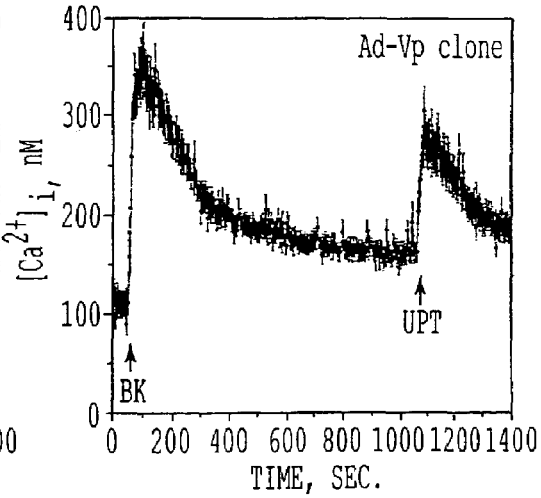
Figure 2E:
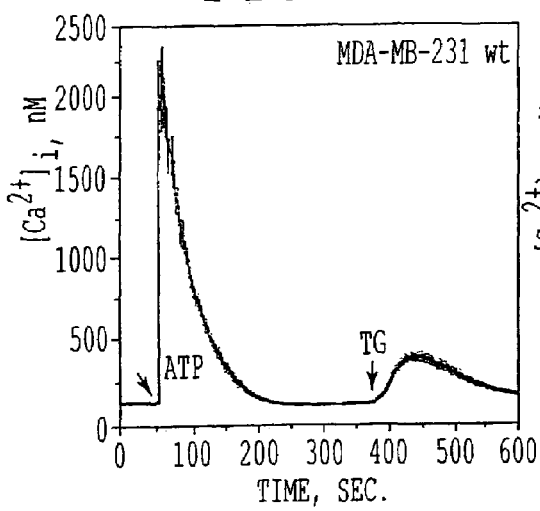
Figure 2F:
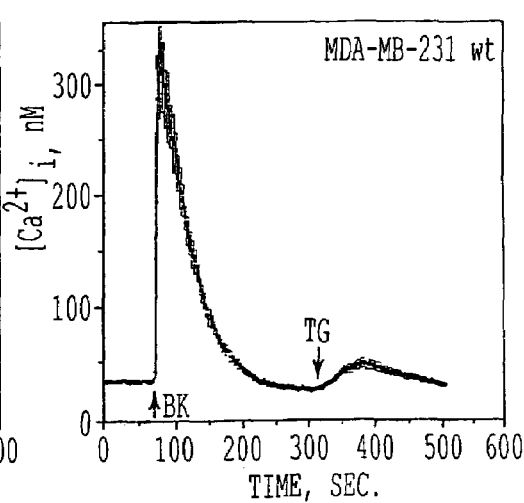
Figure 3A:
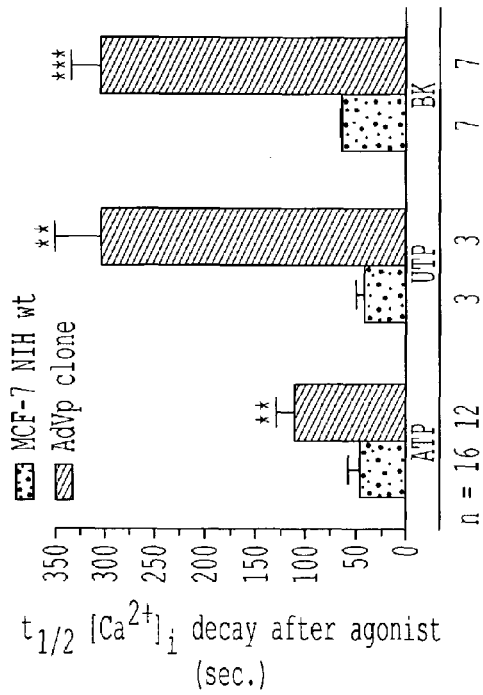
FIGS. 3(a), (b), (c) and (d) provide a summary of $[Ca^{2+}]_1$ decay $t_{1/2}$ in drug-sensitive MCF-7 wt and in drug resistant (DR) breast cancer cells following exposure to various PI-coupled receptor agonists. The darker bars show the $[Ca^{2+}]_1$ decay $t_{1/2}$ for various drug-resistant cancer cells: (a) ADR clone, (b) AdVp clone, (c) C4 and Melph clone and (d) VP clone. The lightly speckled bars appearing on the left of each darker bar show $[Ca^{2+}]_1$ decay for the corresponding parental drug-sensitive MCF-7 cells.
Figure 3B:
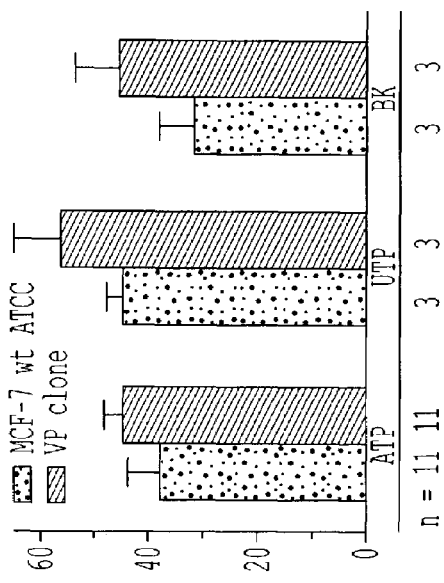
Figure 3C:
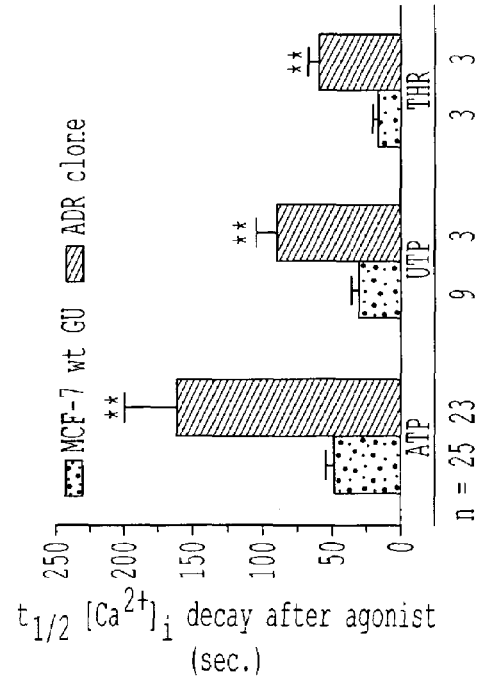
Figure 3D:
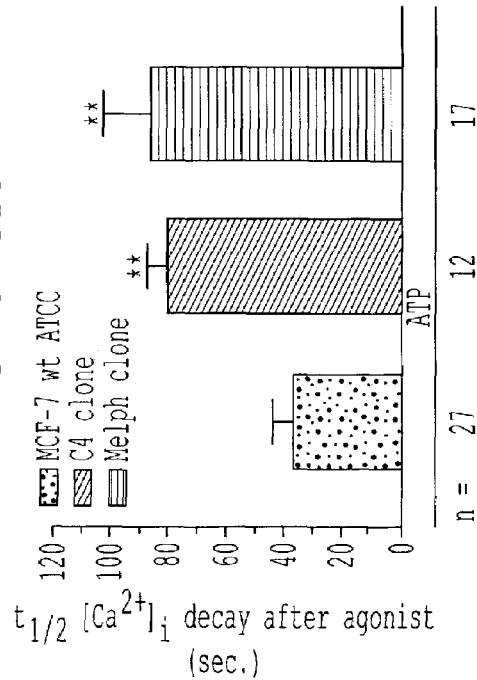

The Ion or Ions measured and analyzed in the methods of the present invention are those ions which are commonly known to be involved in cellular processes and include calcium ions ($Ca^{2+}$), potassium ions ($K^+$), magnesium ions ($Mg^{2+}$), hydrogen ions ($H^+$), sodium ions ($Na^+$), and Chloride ($Cl^-$). Some of these ions, most notably calcium, act as intracellular second messengers, which are involved in, for example, relaying signals inside of the cell based on extracellular stimuli. Therefore, another embodiment provides measuring the cellular dynamics of one or more second messengers to identify drug-resistant and/or drug-sensitive cells on the basis of different dynamics of the second messengers between a drug-sensitive and/or drug-resistant cell. The cellular second messengers include, but are not limited to, for example, $Ca^{2+}$, cyclic nucleotides (such as cAMP and cGMP), protein kinases (such as protein kinase A and protein kinase C), phosphoinositides, diacylglycerol, and nitric oxide.

These ions are analyzed to assess ion dynamics in the cell, which is the temporal and spatial distribution of a particular ion and changes in such distribution within a cell or between a cell and the external environment. Likewise, measuring ion decay kinetics, which is the temporal profile/rate of the decay (return to basal level) of a particular ion after an agonist-induced ionic response, can be used to assess the drug-resistance or drug-sensitivity of a cell.

In another embodiment, anomalous activation rates of response to certain cellular stimuli and/or the overall magnitude of the response in cells that are drug-resistant or drug-sensitive is assessed for the ions and/or second messengers. In addition, these rates of activation and/or magnitude of response can be used to determine the rate at which a cell becomes resistant to a drug.

In several embodiments of the invention, chemosensitizers can be employed, which are agents that are able to reverse drug resistance such that cells resistant to a drug reacquire sensitivity to it. Commonly used chemosensitizers are inhibitor of drug efflux pumps: for example, verapamil and cyclosporin are blockers of the classical MDR pumps—P-gp—while probenecid and genestein are blockers of the MRP pumps. Such agents might include also small peptides, antisense RNAs, and virus-based gene therapeutic agents.

In a preferred embodiment, the second messenger ions measured and analyzed are calcium ions ($Ca^{2+}$).

I. Determining Drug Resistance or Drug Sensitivity of a Cell

The present invention is based on methods for determining drug resistance or drug sensitivity or the level of drug resistance or drug sensitivity of a cell based on analysis of anomalous cellular ion dynamics and/or second messenger dynamics in cells. This method is particularly applicable to cancer cells that are drug resistant. In one embodiment, the method involves measuring cellular ion dynamics, such as calcium flux, release or concentration within different cellular compartments, or into or out of a cell. In another embodiment, the method involves measuring an inability of a cell to restore intracellular ion homeostasis; measuring a difference in sensitivity of a cell or a subcellular compartment to chelation of extracellular ion; measuring a difference in intracellular ion pool sharing; determining the amount of ion in a particular subcellular compartment or organelle, such as the amount of calcium in the endoplasmic reticulum; determining the amount of a particular ion entering or leaving the cell; and/or measuring differences in intracellular ion decay kinetics. In another embodiment, the rates of response activation of the ions/second messengers and/or the magnitude of response to various cellular stimuli are measured to detect anomalous patterns that are correlated to drug-resistance or drug-sensitivity.

In a preferred embodiment, the method involves measuring the intracellular ion decay kinetics of a test cell, such as a cancer cell of a particular tissue type, and comparing the ion decay kinetics with those of one or more control cell(s) of the same tissue type that is drug sensitive. If the ion decay kinetics and/or the cellular second messenger decay kinetics of the test cell (e.g. cancer cell) exhibits a longer decay than the drug sensitive control cell, the test cell is determined to be a drug resistant cancer cell.

Relative intracellular decay rates may also be determined with reference to known controls to assess the relative, or degree of, drug resistance or sensitivity of a test cell. Similarly, one or more known drug-resistant control cells may be used to determine the absolute or relative drug resistance of an unknown cancer cell of the same tissue type. This method may use cancer cells from a cell population of any type of cancer cells or cell lines, and may be applied to cells freshly obtained from tissue removed by biopsy or surgery form a patient. For example, it may be used to detect drug resistance or drug sensitivity in primary cancer cells.

In another embodiment, the method includes identifying those anomalous dynamics relative to preset threshold characteristics of drug sensitive and/or drug resistant cells. For example, the preset threshold characteristic can be derived from analyzing a population of cells and the cellular ion and/or cellular second messenger dynamics whereby one or more anomalous patterns are observed that are consistent with a cell or population of cells exhibiting drug sensitivity and/or drug resistance. The preset threshold can also be determined from published data concerning the dynamics of intracellular ions and/or second messengers.

A drug-resistant cell may exhibit various degrees of anomalous ion/second messenger decay indicative of a slower decay process. As the number of test samples (e.g. various drug resistance cancer cell lines) increases, information on what the limits of confidence are for defining a certain degree of anomaly in decay kinetics as an indicator of acquired drug resistance for that specific cancer cell will become available. For example, compared to drug sensitive MCF-7 cells, the $[Ca^{2+}]_i$ decay $t_{1/2}$ were: ~30% greater (i.e. decay was 30% slower) in MCF-7/VP cells, 100% greater (i.e. decay was twice as slow) in MCF-7/C4 and MCF-7/Melph drug resistant cells. MCF-7/ADR and MCF-7/AdVp drug resistant clones exhibit the slowest decay with an increase in decay $t_{1/2}$ up to ~500%.

In another embodiment of the invention, the methods include comparing a drug sensitive control cell with a test cell, where exhibiting longer intracellular decay kinetics by the test cell compared to those of the drug-sensitive control cell is indicative of drug resistance, or relative drug-resistance, in the test cell. The method may also include the analysis of a control cell, which is drug resistant and the exhibition of shorter intracellular ionic decay kinetics by the test cell compared to those of the drug-resistant control cell is indicative of drug sensitivity, or relative drug-sensitivity, in the test cell.

In a preferred embodiment, the level of drug resistance in a test cell can determined by comparing the ionic/second messenger dynamics of the test cell with those of a drug sensitive control cell and those of a drug-resistant control cell. The degree of resistance may also be determined by comparing the dynamics of the test cell with either the drug sensitive or drug resistant control alone. For example, the intracellular calcium decay half life relative to a test cell compared to known drug sensitive and drug resistant control cells may be used to determine the degree of drug resistance in a test cell.

Determining and comparing ion/second messenger dynamics, such as intracellular ionic decay rates, can also be used to determine the rate at which a cell population acquires resistance to a compound. Similarly, the variation in the decay kinetics may be related to specific drugs and/or mechanisms responsible for drug resistance and to different levels of drug-resistance. Consequently, the degree of drug resistance of two different cancer cell samples may be determined by comparing their respective ionic decay kinetics. As the data presented in this application suggest, a slower calcium decay rate is indicative of a higher level of drug resistance. Preferably, such a comparison is made between a test cancer cell and a control cancer cell known to exhibit no resistance or maximum resistance to one or more drugs. Such methods may also be used to determine the rate at which a cell acquires (or loses) drug resistance by comparing the calcium decay kinetics of sequential samples taken from a cell line exposed (or removed from exposure) to a drug.

To assess relative drug resistance, the ion/second messenger dynamics of a population of cells after a specified period of exposure to a compound can be determined, followed by comparing the dynamics of the cell population to the dynamics of the cell population, or a similar control cell population, obtained prior to the specified period of exposure. The dynamics of the cell population exposed to the compound for a specified period of time are compared to a base line measurement obtained from the cell population prior to exposure to the compound. Examples of compounds used in such a method would be therapeutic drugs or therapeutic drug candidates. Such methods will advantageously determine the rate at which a cancer cell population acquires resistance to particular drugs. This method may include exposing the cell populations to an ion elevating agent and/or a stimulant for a second messenger and comparing the rates of decay of a particular intracellular ion.

The rate at which a cell line loses drug resistance may also be determined by determining the ionic/second messenger dynamics of a population of cells resistant to a compound and then comparing the dynamics of the cell population to the dynamics of the cell population obtained after culturing the resistant population of cells for a specified period in the absence of the compound. The compound may be a therapeutic anticancer drug or drug candidate. The dynamics of the resistant cell population cultured for a specified period in the absence of the compound are compared to a base line measurement obtained from the cell population prior to culturing the cell population in the absence of the compound. In a preferred embodiment, the cell population comprises drug resistant cancer cells, for example, drug resistant breast cancer cells or drug resistant brain cancer cells. In another embodiment, the cell populations are exposed to an ion-specific elevating agent, e.g., calcium elevating agent, and the rates of decay of the intracellular ion are compared. This method may also include labeling the cell populations with an ion sensitive indicator prior to exposure to the elevating agent.

The rates of decay of intracellular ions and/or second messengers for one or both of the compared cell populations may be determined at the time of, or immediately prior to, comparison. The rates of decay of an intracellular ion may be compared by generating a curve representing an ionic level of the drug resistant cell population cultured in the absence of the compound for a specified period, and comparing one or more of the following parameters of the curve: (a) a width of the curve at one-half a maximum amplitude of the curve, (b) a downward slope of the curve from the maximum amplitude to a baseline level; or (c) an area under the curve, with corresponding parameters from a base line measurement obtained from the population of drug resistant cells prior to the specified period. The rates of intracellular decay for one or both of compared cell populations may be a stored curve that is retrieved for comparison, for example, a curve stored as a hard copy or in electronic form. The base line measurement for the cell population prior to exposure to the compound may be generated from stored raw data or generated by direct measurement at the time of or immediately prior to the comparing step.

II. Measuring Ion/Second Messenger Dynamics of a Cell

To measure the ion and/or second messenger dynamics in the methods described herein, various known methods for measuring the concentration of ions in a cell may be employed singularly or in combination. A single ion or second messenger can be measured with one or more methods; or two or more ions/second messengers can be measured simultaneously. Such methods include, but are not limited to, fluorescence measurements, fluorescence resonance energy transfer, bioluminescent measurements, bioluminescence resonance energy transfer, calorimetric measurements, chemoluminescent measurements, and ion-selective microelectrode measurements.

A. Ion Measurements i. Ion-Selective Microelectrodes

Ion-selective microelectrodes can be employed to measure ion flux and ion concentrations in a cell and have the advantage that they can be used non-invasively with respect to the tested cells (Amman (1986) *Ion-selective microelectrodes. Principles, design and application*, Berlin; Springer; Kondo et al (1989) *Pflügers Arch*. 414:663-668; Smith and Trimarchi (2001) *Am. J. Physiol. Cell Physiol*. 280:C1-C11; Gunzel and Schlue (2002) *Biometals* 15(3):237-249; Amman et al (1987) *Can. J. Physiol. Pharmacol*. 65(5):879-884; Meyerhoff and Opdycke (1986) *Adv. Clin Chem* 25:1-47; and Croxton and Armstrong (1992) *Am. J Physiol*. 262(5 Pt 1):C1324-1333). In one embodiment, two or more ion-selective microelectrodes can be used to measure ionic dynamics in a cell or a population of cells relative to a control cell or population of cells. In a preferred embodiment, the ion-selective microelectrode is used to detect calcium dynamics in the cell.

ii. Fluorescent Probes

Ion-specific fluorescent probes are widely used to measure intracellular ion concentrations and ion-fluxes.

Calcium dynamics may be measured by the various techniques known in the art and as described above. These techniques include, but are not limited to fluorescent techniques; radioactive measurement of calcium dynamics may be used, e.g., by measuring $^{45}Ca$ uptake; luminescence assays, e.g. assays using Aequorin, a Ca-sensitive photoprotein; or calcium-mimetic ion fluxes, e.g. assays using a divalent cation, such as magnesium or strontium, which is substituted for calcium in the measurement.

Fluorescence Calcium Imaging is advantageously employed. In addition to other methods known in the art (DeBernardi, M. A., *J. Biol. Chem*. 271:6092-98, 1996), calcium levels may be measured using cell permeable, fluorescent probes sensitive to changes in intracellular calcium concentration to allow one to study the regulation of intracellular free-calcium levels in living cells. Fluorescence-based measurements are fast, usually highly specific, extremely sensitive, and amenable to microscopic detection. The changes in the fluorescence spectrum of these probes are a function of the intracellular concentration of the target being measured, in this case calcium ions. For example, fluorescence techniques involving cell permeable fluorescent dyes (including but not restricted to Fura-2, Fluo-3, Fluo-4, and Indo-1), which are used in fluorimeters (whole cell population response is averaged out) or in fluorescence microscopy (single cell responses is recorded) may be used. Upon binding $Ca^{2+}$, these probes exhibit a quantitative change in the emission intensity measured at the appropriate wavelength(s). Techniques using FRET (Fluorescence Energy Resonance Transfer)-based dyes such as the Camaleons, are probes labeled with two different dyes that, upon binding calcium, undergo conformational changes leading to specific changes in the emission wavelength intensities may also be employed.

Different dyes have distinct spectral characteristics which are affected by increased $Ca^{2+}$ in a specific fashion. The simplest model is a single excitation probe whose fluorescence emission increases when $[Ca^{2+}]_i$ increases (e.g. Fluo-3).

Another model is a probe excitable by two different wavelengths while emitting at the same wavelength such as the most widely used calcium indicator, Fura-2. Upon binding $Ca^{2+}$, the emission coming from the two excitation wavelengths changes in a distinct way with one increasing and the other decreasing as a function of the ion concentration.

Finally, a single excitation probe could be emitting at two different wavelengths whose intensities change as a function of $[Ca^{2+}]_i$ (e.g. Indo-1). The choice of what probe to use depends on a number of factors such as type of cells being grown (e.g. suspension or adherent cultures), instrumentation available (e.g. fluorimeter or microscopic equipment), as well as specific research requirements, such as wavelength compatibility when other fluorescent markers are being used to label the cells.

Other various fluorescent indicators are commonly employed to measure cellular concentrations of ions, as well as ion-flux in the cell. For example, polycarboxylate fluorescent indicators can be employed to measure free metal ion concentrations in cells (Katerinopoulos and Foukaraki (2002) *Curr Med Chem* 9(2):275-306); FURAPTRA is a fluorescent indicator for measuring free magnesium in cells (Raju et al (1989) *Am J Physiol* 256 (3 Pt 1):C540-548; London (1991) *Annu Rev Physiol* 53:241-258); chloride fluorescent indicators such as N-(3-sulfopropyl)quinolinium (Verkman et al (1989) *Anal Biochem* 178(2):355-361; Verkman (1990) *Am J Physiol* 259(3 Pt 1):C375-378); Illsley and Verkman (1987) Biochemistry 26(5): 1215-1219), 6-methoxy-N-(3-sulfopropyl)quinolinium, N-(Ethoxycarbonylmethyl)-6-methoxyquinolinium bromide, 6-Methoxy-N-ethylquinolinium iodide, and Lucigenin; sodium fluorescent indicators such as sodium-binding benzofuran isophthalate and potassium fluorescent indicators such as potassium-binding benzofuran isophthalate (Minta and Tsein (1989) 264(32):19449-19457).

The measurements of the present methods can also include simultaneously determining ion dynamics of different cells within a mixed population of cells. For example, it is possible to label two or more cell populations with a specific colored tag and then co-culture them. Ionic imaging can be performed on the co-cultured cells and single cell responses can be attributed to a distinct population based upon the colored tag. This would provide with an immediate comparison that would have great value because all the cells are being tested under the exact experimental conditions. It is also possible to co-culture DS and DR cells or DR cells with various degrees of resistance and study the ionic dynamics of all of them at the same time in the same sample.

Determining the intracellular ion level(s) can be on a pool of cells floating in a liquid, with only the average response from all the cells being recorded (fluorimetric method); and on monolayers of cells adherent to a surface with single responses from each cell being monitored simultaneously (for example, using a digital imaging method).

Thus, the ionic dynamics of different cell types in a mixed population of cells may be discretely determined at the same time, for example, by the use of different labels or markers for the different cell types.

Ion dynamics, for example, such as the rate of intracellular ion decay can be advantageously determined after exposing the test and control cells to one or more ion elevating agent(s). Such ion elevating agents include ion agonists, for example, agonists which mobilize calcium. The control and test cells may be labeled with a particular ion sensitive indicator prior to exposure of the cells to the one or more of the ion elevating agents.

In a preferred embodiment, the ionic dynamics of the test and control cell(s) may be determined or compared by: (a) determining the intracellular ion decay kinetics of the test cell(s) or control cell(s), or both, after exposure of the cells to one or more ion elevating agent(s), and (b) comparing the decay kinetics of the test cell(s) with those of the control cell(s).

Differences in decay kinetics may be conveniently measured by comparing cytosolic concentration of a particular ionic decay parameters in a drug-resistant cell with that of a drug-sensitive cell. Kinetic parameters may be determined by generating a curve showing intracellular ionic levels over time, before (resting cytosolic concentration of a particular ion) and after agonist addition (onset and decay kinetics). In the curve, the x-axis represents the time and y-axis represents the concentration of the ion. The time (in seconds) when the cytosolic concentration of a particular ion reach 50% of the peak response (maximum amplitude of the curve) is called the onset $t_{1/2}$ and the time that the agonist-increased cytosolic concentration of a particular ion takes to decline to 50% of the peak value while returning to resting levels is called the decay $t_{1/2}$. Decay thus can be determined by measuring the downward slope of the curve from the maximum amplitude to a baseline level or by measuring the area under the curve and comparing such values with similarly calculated values for the corresponding drug-sensitive cells.

One method to determine the degree of correspondence between the ionic dynamics in two cell samples includes determining the cytosolic concentration of a particular ionic decay ($t_{1/2}$) upon application of an ion elevating agent, such as a particular agonist in a drug sensitive cell and then in the cell to be tested. The cytosolic concentration of a particular ionic decay $t_{1/2}$ ($t_{1/2}$) is compared and an increased value in the second tested cell is indicative of drug resistance. Similarly, such a method may involve comparing the decay $t_{1/2}$ of a intracellular ion of a first drug resistant cell and that of a second cell to be tested, where a decrease in the decay $t_{1/2}$ measured in the second cell is indicative of drug sensitivity. Both methods may also be combined and the intracellular ionic decay $t_{1/2}$ of an unknown sample be compared to both a control drug-sensitive and control drug-resistant cell.

iii. Statistical Analyses

Methods for statistical analysis or comparison of patterns representing ion/second messenger dynamics, for example, calcium response magnitude and decay kinetics, are well known in the mathematical and statistical arts. Such methods include two-tailed, unpaired t-test with 95% confidence interval for differences between means (available, for example, through StatMate™, GraphPad Software, Inc. San Diego, Calif.).

iv. Computer Automation

The methods of the present invention may also be implemented on a computer. Values representing the ionic decay kinetics may be encoded in computer-readable form and compared or analyzed by a computer. For example, a computer-readable medium may be encoded with a first set of a plurality of computer-readable values that correspond to data representing the ionic decay kinetics of a first drug-resistant or drug-sensitive cell, or both. The plurality of computer-readable values are arranged such that when retrieved by a processor, the processor is configured to compare the values with a second set of computer-readable values representing the ionic decay kinetics of a second cell to be tested and determine the degree of correspondence between the first set of values and second set of values. The degree of correspondence of the first and second set of values correlate with or is indicative of the degree of drug-resistance or drug-sensitivity in the second test cell.

The invention also encompasses a computer-readable medium encoded with a plurality of computer-readable values that correspond to data representing the ionic decay kinetic profile of a drug-resistant or drug sensitive cell, or both, wherein the plurality of computer-readable values are arranged such that when retrieved by a processor, the processor is configured to present a visual display signal that when input into a display presents a visual representation of the ionic decay kinetics of the cell.

In another embodiment, the computer-readable medium is encoded with a first set of a plurality of computer-readable values that correspond to data representing the ionic decay kinetics of a first drug-resistant or drug-sensitive cell, or both, wherein the plurality of computer-readable values are arranged such that when retrieved by a processor, the processor is configured to compare the values with a second set of computer-readable values representing the ionic decay kinetics of a second cell, and determine the degree of correspondence between the first set of values and second set of values, wherein the degree of correspondence of the first and second set of values correlates with the degree of drug-resistance or drug-sensitivity in the second cell.

v. High-Throughput Screening

The methods for determining or comparing cellular ion/second messenger dynamics of cells or cell populations as described herein may also be applied to high throughput screening for therapeutically useful compounds. High throughput screening (HTS) technology is commonly used to define the rapid processing of cells on a large scale.

vi. Combinatorial Analyses

The analysis of cellular ion/second messenger dynamics to detect drug resistance could be part of a multiplexing assay where other molecules/parameters are monitored simultaneously to provide a multi-sided biochemical signature of the cell reflecting drug resistance or degree of drug resistance. In one embodiment of this combinatorial analysis, two or more ions/second messengers are measured simultaneously or separately for a particular cell population to identify a correlation between cellular ionic dynamics and drug-resistance.

In another embodiment, other second messengers (including but not limited to cyclic AMP, protein kinases, and enzymes) and cellular parameters (including but not limited to cell morphology, viability, apoptosis, and organelle distribution) can be tested in combination to study drug resistance development as well as reversal.

B. Drug Resistance i. Definitions

A drug resistant cell is a cell that has become resistant to a certain chemotherapeutic agent, for example, after a prolonged exposure to the chemotherapeutic agent. A drug sensitive cell is a cell, for example, a cancer cell, that is sensitive to a chemotherapeutic drug applied to it such that the drug is able to limit/stop proliferation of the cell or cancer.

ii. Classes of Drugs/Therapies

A chemotherapeutic agent in cancer therapy is a common description of a drug used in cancer therapy to reduce the rate of cancer cell proliferation, stop cancer cell proliferation, and, in some examples, greatly reduce the number of cancer cells in the patient. Different classes of chemotherapeutic agents are based on various, specific mechanisms of action.

There are those chemotherapeutic agents that affect DNA and/or DNA replication, such as adriamycin which is a DNA intercalating agent, melphalan which is a DNA alkylating agent, VP-16 which is a DNA topoisomerase II inhibitor, and camptothecin which is DNA topoisomerase I inhibitor. Other classes of chemotherapeutic agents are those that inhibit mitotic spindle formation (e.g., Taxol®), aromotase inhibitors (e.g., anastrozole), anthracycline antibiotics (e.g, annamycin), antibody based therapies, and several others. It is common in treating cancer to use combinations of the agents with each other or with other therapies.

iii. Drug Therapy a. Identifying Compounds that Modulate Cellular Ion Dynamics

Determining and comparing cellular ion/second messenger dynamics may also be used for identifying compounds that modulate cellular ion dynamics, for example, those that modulate intracellular ion decay kinetics. Such a method for identifying a compound that modulates ion dynamics of a drug-resistant cell may include comparing the ionic dynamics of a drug-resistant cell before and after contacting the cell with a compound, and selecting a compound that modulates the ionic dynamics of the drug-resistant cell. This method may be applied to cells obtained from cell culture or from biopsies.

Likewise, the effects of particular agents, such as a putative chemosensitizer can be determined by measuring the effects such an agent has on ion/second messenger dynamics, for example, calcium decay kinetics, in a particular cell. In such a case, a comparison is made between a control sample of a drug-resistant cell type with known ion decay kinetics and a test sample of the same cell type exposed to the putative agent. Preferably, the comparison is also made using the decay kinetic profile of a second drug-sensitive cell type. An agent that decreases the intracellular ion decay $t_{1/2}$ in a drug-resistant cell compared to the untreated drug-resistant control is indicative of an agent that may reverse drug resistance.

Similarly, the effects that known chemotherapeutic drugs or drug candidates have on the development of anomalous ion dynamics, such as calcium decay kinetics, can be assessed and a correlation with their ability to induce drug resistance can be obtained. In such a case, the intracellular decay t½ of the ion will be determined at various time points in cancer cells continuously treated, for example, several days and/or months, with the test compound and compared with those in wt, drug untreated cells. The onset of anomalous ionic kinetics suggests the onset of drug resistance. Cell viability/proliferation tests should be performed along with monitoring of ionic kinetics to confirm that cells are indeed killed by the drug, i.e., that they are sensitive to the drug, or the cells survive drug treatment, i.e., the cells are developing drug resistance. In a preferred embodiment, a negative relationship will be observed between the increase in the intracellular ion decay t½, i.e., slower decay kinetics, and the toxicity of the drug being tested, i.e. that more cells survive upon drug treatment and that resistance is developing.

Selection of a compound that modulates cellular ion and/or second messenger dynamics may be based on selecting those compounds that modify the ion dynamics of a drug-resistant cancer cell to be more like those of drug sensitive cells of the same tissue type. For example, when measurements are based on intracellular calcium decay kinetics, a compound may be selected based on its ability to reduce the half-life of intracellular calcium decay in drug resistant cells. Compounds that normalize the calcium decay kinetics of the drug-resistant cell(s) may be selected. The selected compound may be a chemical derivative of a compound such as verapamil, cyclosporin A, probenecid, and genistein. It may also be an MRP modulator or a P-gp modulator.

In addition, HTS technology may also be employed to identify single or multiple cellular targets of a therapeutic drug candidate or compound. This method may comprise contacting multiple drug sensitive or drug resistant cells with multiple candidate chemotherapeutic drugs or chemosensitizers, measuring calcium dynamics of the cells, and selecting a drug or chemosensitizer that alters the calcium dynamics of the drug resistant cells to be more like those of a drug sensitive cell. Thus, HTS technology may be used to screen cells or modulatory compounds on a large scale. For example, the methods described above can be applied on large scale to distinguish cell populations sensitive or resistant to a large variety of different drugs. HTS may also be used to screen candidate chemotherapeutic drugs or chemosensitizers on a large scale on cancer cells of various types and with various degrees of resistance.

b. Cancer Treatment

Compounds identified with the present methods may be formulated as compositions with a pharmaceutically acceptable excipient or carrier, or in combination with other anti-cancer drugs. Such compounds or compositions may be administered by known routes, e.g. orally, parenterally, intravenously, intramuscularly, subcutaneously, or directly to the site of the cancer, to subjects having drug resistant cancer.

A subject having cancer may be treated in conjunction with a determination of the potential degree of resistance of their type of cancer using the methods of the present invention. For example, determining the drug resistance of biopsied cancer cells can be made by determining and comparing the ionic dynamics, e.g., the relative intracellular calcium decay kinetics, of the test cells and appropriate drug sensitive control cells of the corresponding normal tissue from the same subject. Such determinations allow a medical practitioner to either increase the dosage or frequency of administration of an anticancer drug, or both, to a subject having a drug resistant cancer, or alternatively, continue treatment appropriately, when the cancer is determined to have no or a low level of drug resistance. Anticancer treatments based on assessing the degree of drug resistance of a cancer may also comprise administering an adjuvant or a compound that increases the efficacy of the drug to which the cancer cells are resistant or changing the drug regimen. Such information also allows a practitioner to treat a subject with a drug to which the cancer cell is less resistant or to which it is not resistant or to select other appropriate treatments, such as radiation.

Cellular ion/second messenger dynamics may also be used to select a chemotherapeutic drug that acts via a mechanism not involving the alteration of the dynamics. Such a method may comprise contacting a drug sensitive cancer cell with a chemotherapeutic drug for a series of increasing periods of time, monitoring and comparing ionic dynamics of the cells at each period of time, and selecting a chemotherapeutic drug that reduces growth rate of the drug sensitive cancer cell without altering these ionic dynamics of the cell.

III. Kits

The present invention also embodies kits for determining the ion/second messenger kinetics, e.g., decay kinetics, of a cell sample and can include, for example, a drug sensitive cell sample; an ion-sensitive label for labeling cells; and a ion elevating agent, for example, an agonist for calcium mobilization. These kits can also contain an ion-sensitive label, which may be a fluorescent label.

Kits for screening a chemosensitizer that reverses cellular drug resistance may include a sample of drug resistant cells having a measurable level of drug resistance; a calcium sensitive label for labeling cells; and an agonist for calcium mobilization for the drug resistant cells. Such a kit may comprise a sample of drug sensitive cells of a same tissue type as the drug resistant cells and the calcium sensitive label may be a fluorescent label.

Having generally described this invention, a further understanding can be obtained by reference to certain specific examples which are provided herein for purposes of illustration only and are not intended to be limiting unless otherwise specified.

EXAMPLES

More specifically, human breast cancer cell ("bc") lines were obtained from the following sources: wild type ("wt"), estrogen receptor-positive MCF-7 cells were obtained from three different sources: American Type Culture Collection (ATCC, Manassas, Va.), the Lombardi Cancer Center, Georgetown University (Washington, D.C.) and the National Cancer Institute, NIH (Bethesda, Md.) and will be referred to as "wt", DS MCF-7 throughout the paper. Wild type, estrogen receptor-negative MDA-MB-231 cells were obtained from the Lombardi Cancer Center, Georgetown University. Five DR, MCF-7-derived clonal cell lines were used in this study. MCF-7/ADR (selected by exposure and resistance to adriamycin, a DNA intercalating agent and DNA topoisomerase II inhibitor; (Vickers, P. J. et al. *Mol. Endocrinol.* 2:886-892, 1988) were from the Lombardi Cancer Center, Georgetown University; MCF-7/C4 (selected, after mutagenesis, for resistance to camptothecin, a DNA topoisomerase I inhibitor) were obtained from Dr. Y. Pommier (NCI, NIH, Bethesda, Md.) (Fujimori, A. et al. *Mol. Pharmacol.* 50:1472-1478, 1996); MCF-7/VP cells (selected by exposure and resistance to VP-16 etoposide, a DNA topoisomerase II inhibitor; Schneider, E. et al. *Cancer Res.* 54:152-158, 1994) were obtained from Dr. E. Schneider, Wadsworth Center, New York State Dept. of Health, Albany, N.Y.; MCF-7/Melph cells (selected by exposure and resistance to melphalan, a DNA alkylating agent; Moscow, J A et al. *Br. J. Cancer* 68:732-737, 1993) were obtained from Dr. J. Moscow, University of Kentucky, Lexington, Ky. (25); and MCF-7 Ad/Vp 3000 cells (selected by exposure to adriamycin and verapamil; Lee, J. S. et al. *J. Cell. Biochem.* 65:513-526, 1997) and their parental wt, DS MCF-7 line were from Dr. S. Bates, National Cancer Institute, NIH, Bethesda, Md. MCF-7/ADR cells over-express P-gp, MCF-7/VP cells over-express MRP, MCF-7/C4 and MCF-7/Melph cells are not known to over-express either P-gp or MRP, MCF-7/Ad-Vp cells do not over-express P-gp or MRP, but express BCRP (Doyle, L. A. et al. *Proc Natl Acad Sci, U.S.A.* 26:15665-670, 1998).

C6 rat glioblastoma cell lines: Wild type cells and progressively doxorubicin-resistant clones were obtained from Dr. J. Robert, Institute Bergonie, Bordeaux, France. Clones were selected by exposure to increasing doses of doxorubicin: Clone A, 0.001 µg/ml; Clone B, 0.1 µg/ml, and Clone E, 0.5 µg/ml. All three clones overexpress P-gp but the drug resistant phenotype is totally reversed by verapamil only in Clone A (Huet, S. et al. *Br. J. Cancer*: 65:538-44, 1992).

Cell Culture Techniques. The following cell culture conditions were used:

Cells were grown at 37° C. in a humidified atmosphere of 95% air/5% $CO_2$. All bcc lines except MCF-7/C4 were grown in IMEM medium supplemented with 10% fetal calf serum, 2 mM L-glutamine, 100 U/ml penicillin, 100 ug/ml streptomycin and 50 ug/ml gentamycin. MCF-7/C4 were grown in RPMI-1640 with 5% fetal calf serum, 1 mM nonessential amino acids, 0.1 mM sodium pyruvate, 2 mM glutamine, 100 U/ml penicillin, 100 ug/ml streptomycin and 50 ug/ml gentamycin. C6 cells were grown in DMEM medium supplemented with 10% fetal calf serum, 2 mM L-glutamine, 100 U/ml penicillin, 100 ug/ml streptomycin and 50 ug/ml gentamycin. Media, serum and cell culture reagents were from Biofluids, Inc., Rockville, Md. DR clones were grown in the presence of the appropriate drug: MCF-7/ADR=2 uM doxorubicin; MCF-7NVP=4 uM VP-16 etoposide, MCF-7/Melph=6 uM melphalan; MCF-7/Ad-Vp 3000=5 uM doxorubicin and 10 uM verapamil; C6 clones: see above. All drugs were purchased from Sigma, St. Louis, Mo.

For data mentioned below, $[Ca^{2+}]_i$ was measured by single-cell fura-2 excitation ratio imaging as previously described (DeBernardi, M. A. et al. Mol Pharmacol 43:451-58, 1993). Cells, grown on 25 mm round, 1 mm-thick glass coverslips were loaded with cell-permeable fura-2 AM (5 uM; Molecular Probes, Eugene, Oreg.) at 37° C. in growth medium for 30-60 min. MCF-7/ADR, MCF-7/Ad-Vp, and C6-B and E cells were difficult to load with fura-2 AM, likely reflecting a high degree of dye extrusion (Homolya, L. et al. J Biol. Chem. 268:21493-96, 1993). In experiments where a pre-treatment with VER (25 uM) or CSA (100 uM) was called for, an improved loading of the dye in MCF-7/ADR cells was observed (Homolya et al *J Biol Chem* 268:21493-96, 1993). Cells were then thoroughly washed with buffer H/H (Ham's F-10 nutrient mixture supplemented with 20 mM Na-HEPES, pH 7.4) and let sit for 10 min at room temperature to allow complete fura-2 AM de-esterification. Cells were imaged at room temperature in H/H buffer using an Attofluor RatioVision Digital Fluorescence Microscopy System (Atto Bioscience, Rockville, Md.) equipped with a Zeiss Axiovert 135 microscope and a F-Fluar 40×, 1.3 na, oil-immersion objective. Fura-2 was excited at 334 and 380 nm with the emission monitored at >510 nm; the 334/380 nm excitation ratio increases as a function of the $[Ca^{2+}]_1$. Calibration was done in vitro with 10 uM fura-2 pentapotassium salt in the presence of 1 mM $CaCl_2$ or 1 mM EGTA and the 334/380 nm excitation ratio was converted to $[Ca^{2+}]_1$ nM values (Grynkiewicz et al *J Biol Chem* 260:3440-3450, 1985). For each coverslip, 10-99 cells were simultaneously imaged in a given microscopic field and $[Ca^{2+}]_1$ was recorded from each individual cell in resting and stimulated conditions. Single $Ca^{2+}$ profiles were averaged to yield $[Ca^{2+}]_1$ population means (±S.E.M.) that were plotted versus time. Statistical analyses used the two-tailed, unpaired t-test with 95% confidence interval for differences between means (StatMate™, GraphPad Software, Inc., San Diego, Calif.).

EXAMPLE 1

HUMAN BREAST CANCER CELLS EXHIBIT ALTERED $[Ca^{2+}]_1$ DYNAMICS

The inventors have identified differences in $Ca^{2+}$ dynamics of agonist-induced $Ca^{2+}$ responses between human breast cancer cells including MCF-7 and MDA-MB-231 wt that had never been exposed to anti-cancer drugs and five MCF-7 derived drug-resistant (DR) clones.

Single cell $Ca^{2+}$ dynamics were monitored by single cell fluorescence digital imaging according to the method previously described by DeBernardi, M. A. et al. *Mol Phamacol* 43: 451-458 (1993). Cells were grown as monolayers on glass supports and labeled with the cell-permeable fluorescent dye, Fura-2 (Molecular Probes, Inc.).

Basal $[Ca^{2+}]_1$ levels and responses to ATP (50-100 uM), UTP (50-100 uM), BK (10 uM), THR (5 uM), or TG (1 uM) were studied in single cells. The rational for using these compounds was to separately study: i) $Ca^{2+}$ mobilization from intracellular stores via activation of $IP_3$ receptors [ATP, UTP, BK, THR are PI-coupled receptor agonists which activate IP3 receptors and $Ca^{2+}_1$ release, Dixon et al *Br J Cancer* 75:34-9, 1997; Yang et al *Br J Pharmacol* 112:781-8,1994; Panettierl et al *Am J Respir Cell Mol Biol*], ii) $Ca^{2+}$ release from intracellular stores by-passing the PI pathway [TG poisons $Ca^{2+}$-ATPase pumps of the endoplasmic reticulum preventing the re-uptake into the stores of $Ca^{2+}$ passively diffused out into the cytosol]. $Ca^{2+}$ responses were compared between pairs of DS and DR clones tested in parallel (MCF-7/ADR cells were compared to their parental wt, DS line obtained from Georgetown University; MCF-7/Ad-Vp cells were compared to the NIH wt, DS line; other DR clones were compared mainly with wt, DS MCF-7 cells from ATCC; C6 clones resistant to doxorubicin were compared to their wild type parental line.

Basal $[Ca^{2+}]_1$ levels: Resting $[Ca^{2+}]_1$ was recorded for about 60 sec. before stimulation with drugs and ranged between 30 and 100 nM. Resting $[Ca^{2+}]_1$ of the MCF-7 cell derived DR clones tested in this study were not significantly different from those of their wt DS cells, although the DR clones exhibited a wider range of variability (Table 1).

TABLE 1

Basal $[Ca^{2+}]_i$ (nM) in Various Breast Cancer Cell Lines

| Wild Type Drug-sensitive Cells | | |
|---|---|---|
| MCF-7 GU[a] | 45.1 ± 13.4[b] | n[c] = 48 |
| MCF-7 NIH | 50.5 ± 8.5 | n = 32 |
| MCF-7 ATCC | 53.5 ± 10.2 | n = 30 |
| MDA-MB-231 | 35.8 ± 11.2 | n = 15 |
| Drug-resistant Cells | | |
| MCF-7/ADR | 60.5 ± 10.2 | n = 38 |
| MCF-7/Ad-Vp | 57.5 ± 19.5 | n = 33 |
| MCF-7/VP | 49.6 ± 22.0 | n = 14 |
| MCF-7/C4 | 70.1 ± 12.2 | n = 20 |
| MCF-7/Meph | 77.0 ± 27.0 | n = 24 |

Upon stimulation with various PI-coupled receptor-agonists, $Ca^{2+}$ responses were similar in magnitude and onset kinetics among DS and DR MCF-7 cells. However, the decay kinetics, which reflect the ability of the cells to re-establish $Ca^{2+}_1$ homeostasis after $[Ca^{2+}]_1$ is increased, were considerably slower in DR clones compared to DS cells (FIGS. 1, 2 and 3, Table 2).

TABLE 2

Fold $[Ca^{2+}]_1$ Increase Evoked by Various Agonists in Human Breast Cancer Cell Lines

| Agonist | ATP | UTP | BK | THR | TG |
|---|---|---|---|---|---|
| Drug-sensitive Cells | | | | | |
| MCF-7 wt | 7.9 ± 1.8[a] (n = 67) | 6.0 ± 1.3 (n = 9) | 4.1 ± .8 (n-16) | 2.8 ± 0.1 (n = 3) | 2.8 ± 0.5 (n = 21) |
| MDA-MB-231 | 16.5 ± 4.8 (n = 10) | n.d.[b] | n.d. | 13.5 ± 5.1 (n = 3) | 3.5 ± 0.9 (n = 3) |
| Drug-resistant Cells | | | | | |
| MCF-7/ADR | 2.9 ± 0.7 (n = 25) | 2.2 ± 0.3 (n = 3) | 1.9 ± 0.5 (n = 3) | 2.8 ± 1.1 (n = 3) | 2.7 ± 0.7 (n = 10) |
| MCF-7/AdVp | 4.5 ± 1.2 (n = 12) | 3.7 ± 0.8 (n = 3) | 3.5 ± 1.0 (n = 7) | n.d. | 2.4 ± 0.7 (n = 11) |
| MCF-7/VP | 4.4 ± 1.2 (n = 11) | 5.2 ± 1.9 (n = 3) | 3.3 ± 1.7 (n = 3) | n.d. | 1.5 ± 0.1 (n = 6) |

TABLE 2-continued

Fold $[Ca^{2+}]_i$ Increase Evoked by Various Agonists in Human Breast Cancer Cell Lines

| Agonist | ATP | UTP | BK | THR | TG |
|---|---|---|---|---|---|
| MCF-7/C4 | 5.9 ± 0.8 (n = 12) | n.d. | 3.0 ± 0.6 (n = 3) | 3.3 ± 0.3 (n = 3) | 3.4 ± 0.8 (n = 7) |
| MCF-7Melph | 16.0 ± 6.1 (n = 17) | 3.7 ± 0.3 (n = 5) | n.d. | n.d. | n.d. |

[a]Mean ± S.E.M.;
[b]not determined

Cells were labeled with Fura-2 and imaged. After 30-60 sec., the agonists were applied and calcium responses were recorded in single cells. The fold increase in $[Ca^{2+}]_i$ were calculated and the average values from all the experiments were used in this table. Variations in the magnitude of the Ca responses between DS and DR were observed with some agonists inducing greater responses in DS than in DR cells.

Figure 4A:
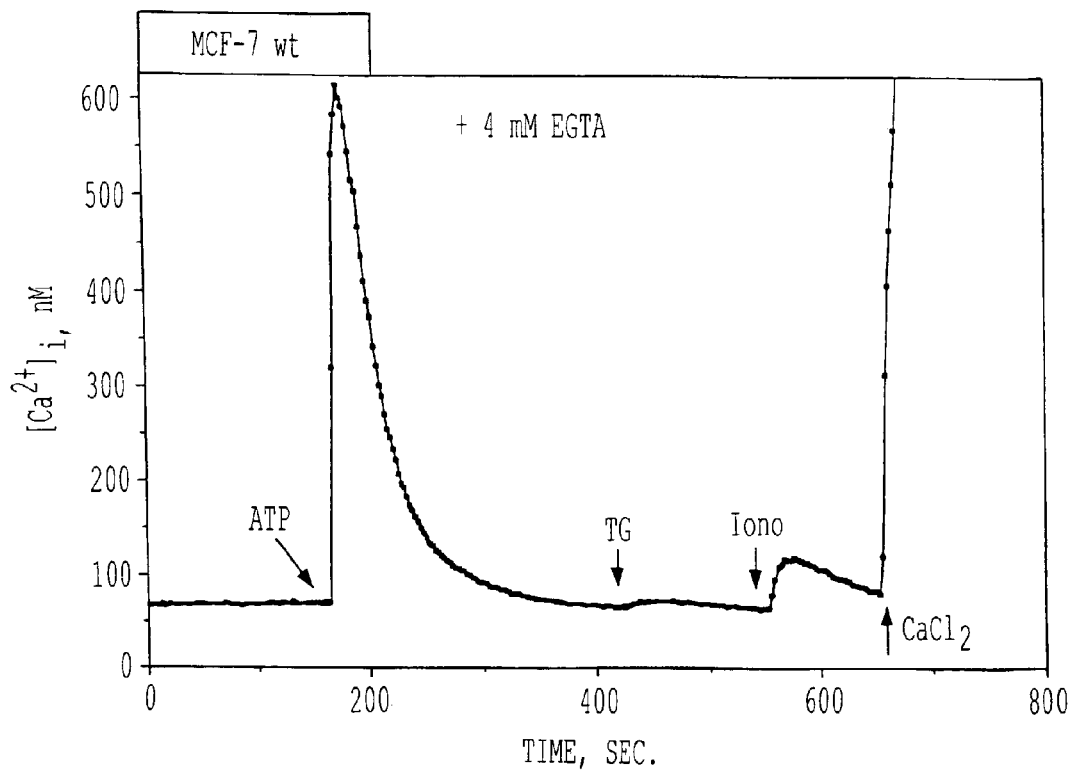
FIGS. 4(a) and (b) show ATP-induced $[Ca^{2+}]_1$ increase in drug-sensitive MCF-7 wt and drug-resistant MCF-7/ADR cells in the presence of EGTA in the extracellular milieu. EGTA binds to and sequesters calcium ion thus preventing calcium entry into the cells. Even in the absence of extracellular calcium, drug-resistant clones exhibit a longer $[Ca^{2+}]_1$ decay than wt cells and a response to TG after ATP.
Figure 4B:
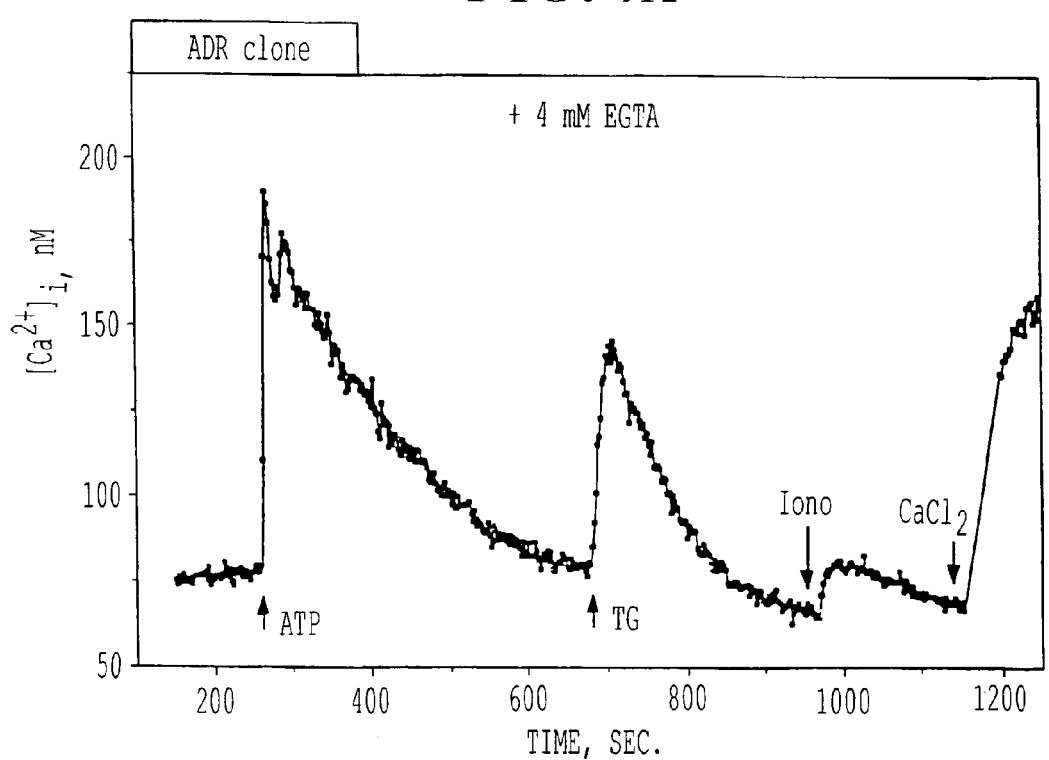
Figure 5A:
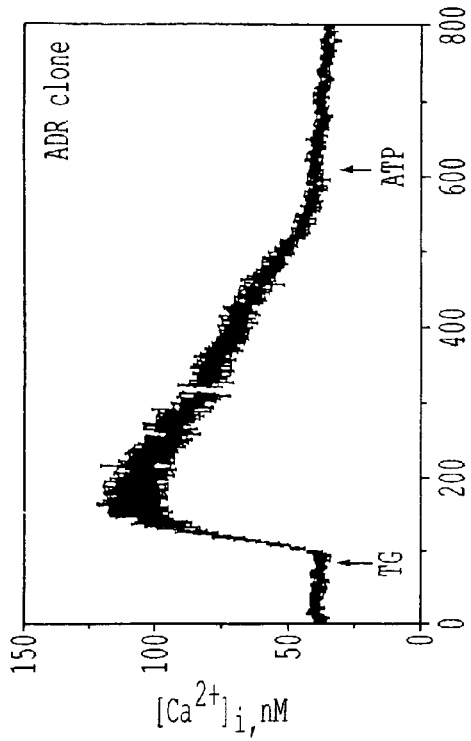
FIGS. 5(a), (b), (c) and (d) show the $[Ca^{2+}]_1$ increase evoked by TG when applied to the cells as the first drug to drug-sensitive MCF-7 wt (a) and drug-resistant clones ADR (b), C4 (c) and Ad-Vp (d). TG inhibits the re-uptake of the ion—that passively diffuses out of the stores—back into such stores; the stores are thus depleted of $Ca^{2+}$ and this prevents a subsequent $Ca^{2+}$ release by ATP.
Figure 5B:
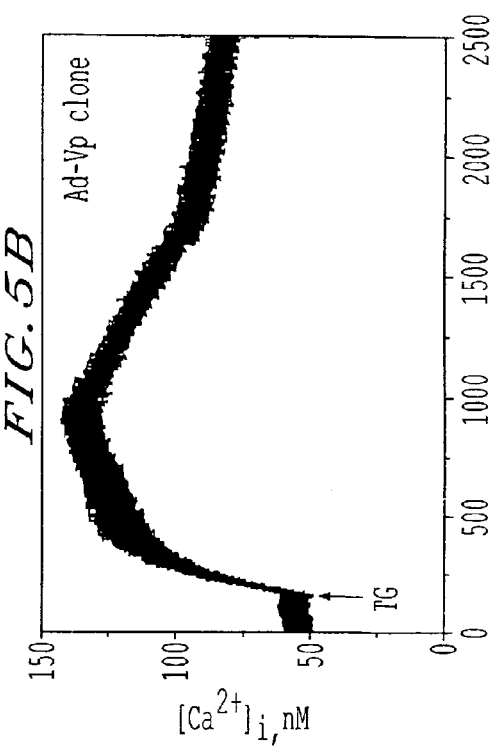
Figure 5C:
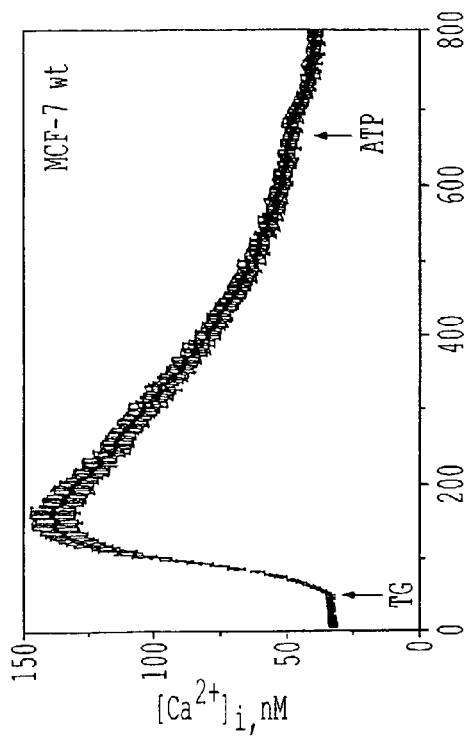
Figure 5D:
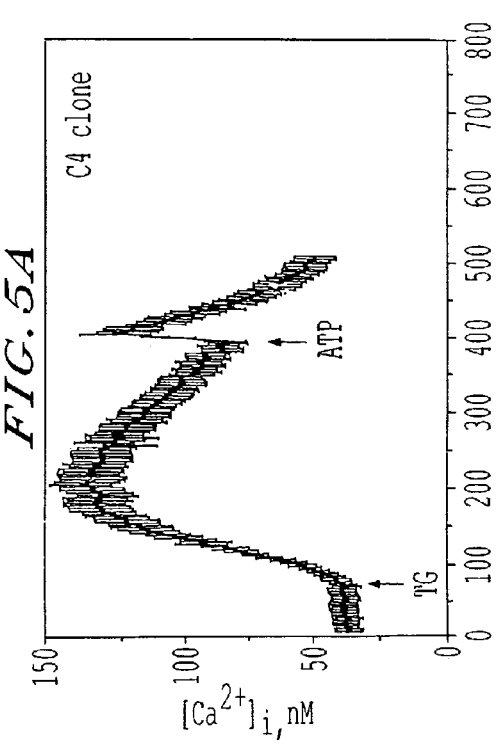

Following a stimulus-induced $[Ca^{2+}]_i$ increase, cells rectify their $[Ca^{2+}]_i$ by extruding the ion through ATP-powered $Ca^{2+}$ pumps on the plasma membrane, re-uptaking it into intracellular stores via endoplasmic reticulum $Ca^{2+}$-ATPase pumps, and sequestering it through binding to cytoplasmic $Ca^{2+}$-binding proteins. When the extra-cellular concentration of $Ca^{2+}$ is virtually zero, as in the presence of the $Ca^{2+}$ chelator EGTA, the return of agonist-increased $[Ca^{2+}]_i$ to resting levels is faster because i) the capacitative $Ca^{2+}$ entry, triggered by agonist-induced depletion of the stores (Berridge, M.J. Nature, 361:315-325, 1993), does not occur and ii) the efflux of the ion, accumulated in the cytosol, from the cells is facilitated by virtue of a favorable gradient. Experiments performed in the absence of $Ca^{2+}_e$, showed indeed a faster decay of the agonist-increased $[Ca^{2+}]_i$ in both DS and DR cells; however, DR cells remained slower than DS cells in lowering their $[Ca^{2+}]_i$ after receptor stimulation (FIG. 4, Table 3). These results indicate that the longer $[Ca^{2+}]_i$ decay observed in DR cells in standard $Ca^{2+}$ conditions, is not due to a capacitative $Ca^{2+}$ influx more sustained in DR cells than in wt cells.

TABLE 3

Effect of the absence of extracellular $Ca^{2+}$ on the ATP-evoked $Ca^{2+}$ response

| | Standard Buffer | | EGTA-containing Buffer | |
|---|---|---|---|---|
| | $[Ca^{2+}]_i$, fold increase | Decay $t_{1/2}$(sec.) | $[Ca^{2+}]_i$, fold increase | Decay $t_{1/2}$(sec.) |
| Drug-sensitive cells | | | | |
| MCF-7 wt[a] | 8.1 ± 2.4[b] (n = 13) | 51.3 ± 7.0 | 6.2 ± 2.1 (n = 6) | 31.8 ± 9.0 |
| MDA-MB-231 | 16.5 ± 4.8 (n = 10) | 46.7 ± 5.3 | 26.0 ± 8.1 (n = 3) | 29.0 ± 5.6 |
| Drug-resistant cells | | | | |
| MCF-7/ADR | 3.7 ± 0.7 (n = 13) | 206.7 ± 57.0[*c] | 2.4 ± 0.3 (n = 5) | 76.0 ± 9.6[**d] |
| MCF-7/C4 | 5.8 ± 0.9 (n = 12) | 79.3 ± 8.5[*e] | 4.9 ± 0.4 (n = 3) | 32.0 ± 3.3 |

[a]Data from wt cells represent the average responses from all the three MCF-7 wt cell lines utilized in this set of experiments.
[b]Data represent means ± S.E.M.
*P < 0.05,
**P = 0.01 t-test;
[c,e]significantly different from decay $t_{1/2}$ of MCF-7 wt cells in standard buffer;
[d]significantly different from decay $t_{1/2}$ of MCF-7 wt cells in EGTA-containing buffer.

Cells were loaded with Fura-2 and imaged in the absence or presence of EGTA, which is a calcium chelator. Cells were challenged with ATP and Ca responses were recorded. The magnitude and decay $t_{1/2}$ of the responses were calculated and the respective mean of all the experiments was compared. No statistically significant differences were observed between Ca increases in DS and DR cells showing that the ATP-induced Ca increase is primary due to Ca release from the store rather than Ca entry from the outside. Decay kinetics were faster in the presence of EGTA because capacitative Ca entry does not occur in the absence of extracellular calcium. However, even in the presence of EGTA, decay kinetics of MCF-7/ADR cells were slower than those of wt DS cells.

TG leads to $[Ca^{2+}]_i$ increase and depletion of internal stores by preventing the re-uptake of $Ca^{2+}$, constitutively leaking from the stores, back into the lumen of the endoplasmic reticulum. The magnitude and onset kinetics of the $[Ca^{2+}]_i$ rise evoked by TG were similar in DS and DR cells (FIG. 5, Table 2) suggesting the presence of comparably filled TG-releasable $Ca^{2+}$ pools, similar $Ca^{2+}$ ATP-ase pump activity, and comparable $Ca^{2+}$ leakage from these stores into the cytosol.

When the reuptake of the ion is prevented by TG, physiological $[Ca^{2+}]_i$ can be re-established by the cells through enhanced $Ca^{2+}$ efflux or binding to $Ca^{2+}$ binding proteins. In two DR clones, MCF-7/VP and MCF-7/Ad-Vp cells, the decay of the $Ca^{2+}$ response induced by TG was significantly slower than DS cells, suggesting differences in the way DR and DS cells cope with IP3 receptor-independent increases in $[Ca^{2+}]_i$. Interestingly, in DR clones, but not in MCF-7 wt or MCF-7/Vp cells (the only DR clone exhibiting receptor-mediated $[Ca^{2+}]_i$ decay similar to wt cells), TG increased $[Ca^{2+}]_i$ when applied after ATP, regardless of the magnitude of the preceding ATP-evoked $Ca^{2+}$ response. These results might imply that TG- and $IP_3$-releasable $Ca^{2+}$ stores are differentially shared in DS and DR MCF-7cells and exhibit different sensitivity to $Ca^{2+}_e$. Surprisingly, in three DR clones but not in DS cells, a first challenge with TG failed to prevent a subsequent $[Ca^{2+}]_1$ increase by ATP, suggesting differences in sensitivity to TG of the $Ca^{2+}$ uptake pumps of DS and DR cells. Indeed, $IP_3$-releasable $Ca^{2+}$ pools whose pumping activity is resistant to TG have been reported in a line of Chinese hamster lung fibroblasts (Waldron RT et al. *J Biol Chem* 272:6440-6447, 1997).

Cytoplasmic $Ca^{2+}$-binding proteins function either as buffers or as sensors to carry out the messenger role of $Ca^{2+}$. Most of the $Ca^{2+}$ accumulating within the cytoplasm in response to a stimulus is bound to these buffers with the small remainder representing the actual second messenger. Thus, a reduced availability of $Ca^{2+}$-binding proteins or a decreased affinity for $Ca^{2+}$ could result, in the absence of a compensatory efflux, in a prolonged elevation of $[Ca^{2+}]_1$ and slower recovery of homeostatic $Ca^{2+}_i$ levels. The DR lines studied were found to be indeed slower compared to their parental DS cells in re-establish resting $[Ca^{2+}]_1$. Recent reports show either up- or down-regulation of various $Ca^{2+}$-binding proteins in human breast cancer with no differential expression between DS and DR cells. Changes in the expression, subcellular distribution or affinity for $Ca^{2+}$ of cytoplasmic $Ca^{2+}$-binding proteins may play a role in the altered regulation of Ca2+ homeostasis in DR cells.

Figures 6A, 6B:
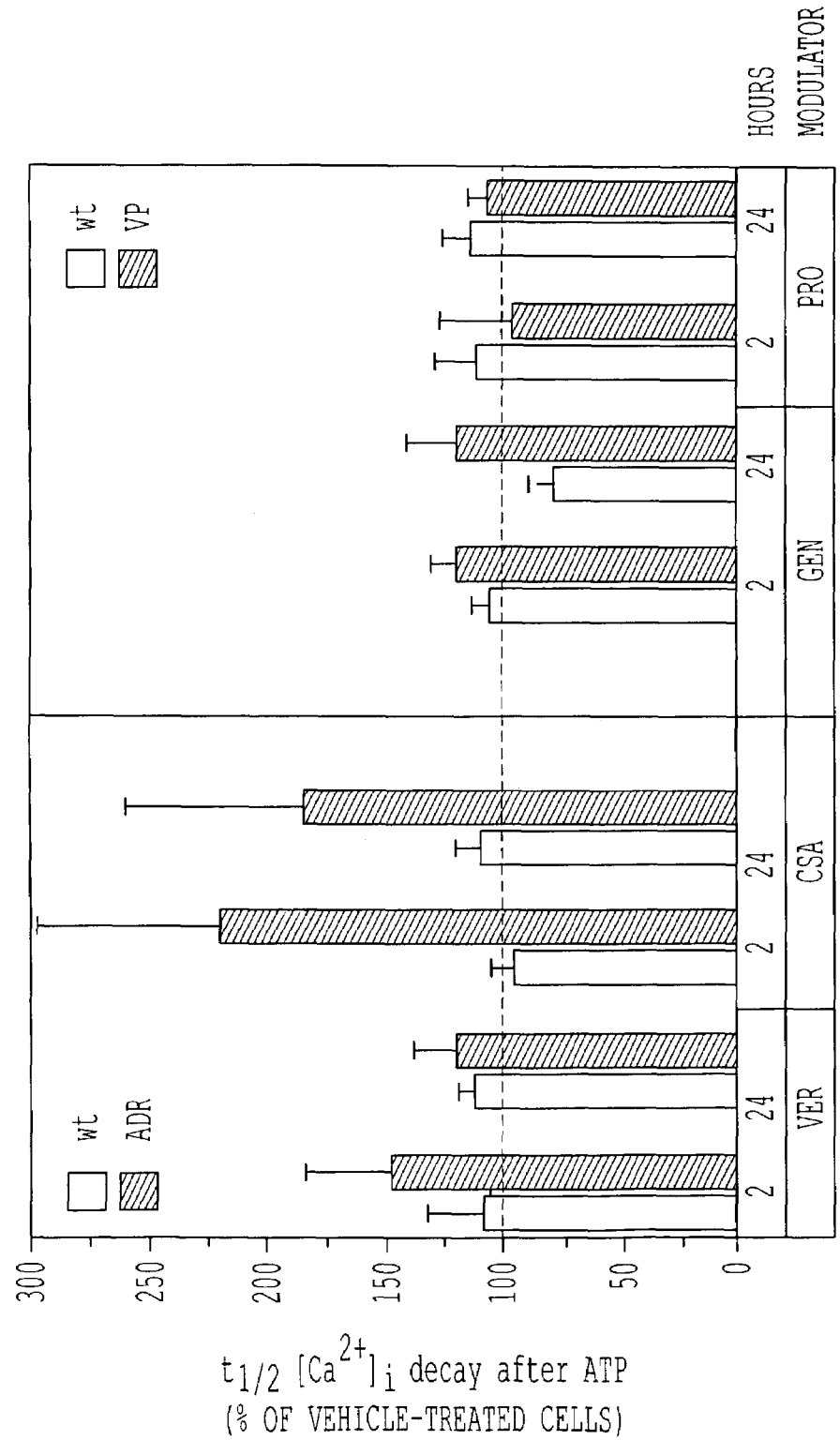
FIGS. 6(a) and (b) show the lack of effect of P-gp and MRP modulators, VER (verapamil), CSA (cyclosporin A), GEN (genistein) and PRO (probenecid) on the decay of the ATP-evoked $[Ca^{2+}]_1$ increase in drug-sensitive and drug-resistant MCF-7 cells. These data show that drug resistant cells maintain a significantly longer $[Ca^{2+}]_1$ decay than wild type drug-sensitive cells in the presence of inhibitors or P-gp and MRP pumps.
Figure 7:
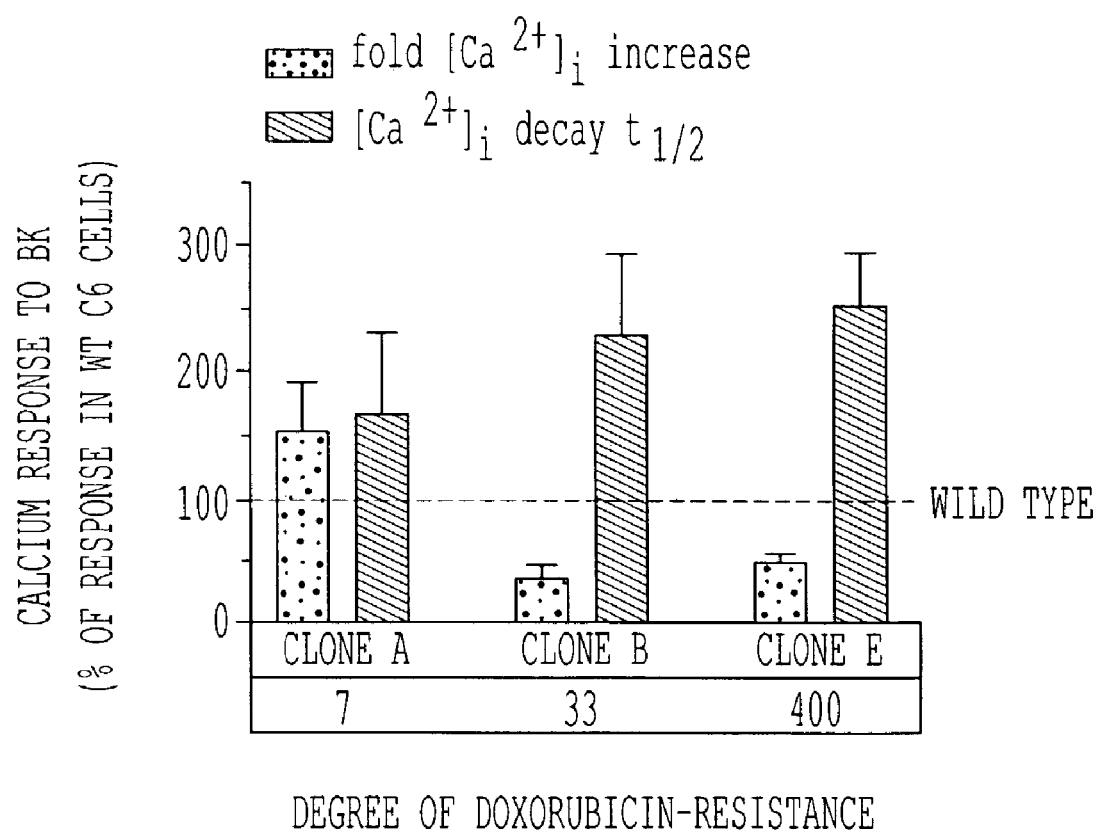
FIG. 7 shows $Ca^{2+}$ responses (fold $[Ca^{2+}]_1$ increase and decay $t_{1/2}$) evoked by BK in C6 wt, drug sensitive cells and adriamycin-resistant clones derived from wt. Data are normalized and presented as percent of the response detected in wild type C6 cells, i.e. this response is considered as being 100%. Clones B and E, which exhibit higher drug resistance than clone A, also exhibit longer calcium decay and a calcium increase of lesser magnitude than clone A.

Finally, the changes in $Ca^{2+}$ handling observed in DR cells do not apparently correlate with the functional expression of classical multi-drug resistance associated drug efflux pumps (FIG. 6). Indeed, P-gp and MRP modulators failed to accelerate the $[Ca^{2+}]_1$ decay of the ATP-evoked $Ca^{2+}$ response in P-gp-expressing ADR cells (Fairchild, CR et al. *Cancer Res* 47:5141-5148, 1987) and MRP-expressing VP cells (Schneider, E. et al. *Cancer Res* 54:152-158, 1994), respectively. Importantly, in MCF-7/ADR cells, the P-gp modulators VER and CSA greatly improved fura-2 loading and enhanced the magnitude of the ATP-evoked $Ca^{2+}$ response, but were not able to modify the decay kinetics of such responses. These results, together with the finding that DR cells expressing neither of the classical drug efflux pumps—such as the Ad-Vp, C4, and Melph clones—also show a longer $[Ca^{2+}]_i$ decay, disfavor a causal relationship between the over-expression of these pumps and the anomalous $[Ca^{2+}]_1$ decay.

While the physiological implications of the slower $[Ca^{2+}]_i$ decay in the mechanisms of drug-resistance can only be speculated upon at the present time, numerous are the biological systems wherein changes in $Ca^{2+}_i$ homeostasis at various stages of differentiation have been reported.

EXAMPLE 2

DRUG-RESISTANT RAT BRAIN TUMOR CELLS EXHIBIT ALTERED CALCIUM DECAY DYNAMICS

Four C6 rat astrocytoma cell lines were tested: the wild type, DS parental cells, and 3 DR clones A, B and E obtained by selection with increasing doses of adriamycin and exhibiting increasing degree of resistance to the drug (7, 33, and 400 fold resistance, respectively). This means that the dose of adriamycin necessary to kill 50% of the DR cells was 7, 33, 400 times greater in clone A, B, C, respectively, than the dose necessary to kill 50% of the wt, DS cells.

Experiments were performed essentially as described above for MCF-7 cells. However, BK was chosen as a routine Ca agonist because not all the lines responded consistently to ATP. To accurately compare the various lines, parental cells and all clones were plated on the same day and calcium imaging was performed on all the cell lines on the same day. Clones A and E showed the highest percentage of cells responding to BK; clone A exhibited a quantitative $[Ca^{2+}]_1$ increase comparable or greater than C6 parental cells while clone E as well as clone B showed a reduced response. Clone B was the only clone to respond consistently to ATP even when applied after BK. Importantly, a positive correlation was observed between the degree of resistance to doxorubicin expressed by the three clones and their $([Ca^{2+}]_1$ decay $t_{1/2}$. In clone A, which exhibits the lowest degree of drug resistance, $[Ca^{2+}]_1$ decay kinetics were found to be slightly slower than wild type cells ($[Ca^{2+}]_1$ decay $t_{1/2}$: 167±63% of parental cells) whereas they were significantly slower in clones B (228±84%; intermediate degree of drug resistance) and E (250±41%; highest degree of drug resistance). All the cell lines responded to TG when applied either before or after BK and ATP; clone A showed a greater TG-induced $[Ca^{2+}]_1$ increase than parental cells while clone B and E exhibited a much reduced response. In all the clones, the $[Ca^{2+}]_1$ decay kinetics after TG stimulation were comparable or faster than wild type cells.

EXAMPLE 3

ONSET KINETICS OF RECEPTOR-STIMULATED $[Ca^{2+}]_1$ INCREASE IN BREAST CANCER CELLS

Human breast cancer cells loaded with Fura-2, were exposed to various agonists and $[Ca^{2+}]_1$ responses from single cells were recorded. The number of cells responsive to a given agonist varied among the various cell lines. In both DS and DR cells, ATP and UTP consistently evoked $Ca^{2+}$ responses in >95% of the cells being imaged (and, thus, they were used to carry out the majority of the experiments) while THR and BK induced $Ca^{2+}$ responses in a smaller number of cells (<30%). The magnitude of the peak $[Ca^{2+}]_i$ responses also varied among DS and DR cells depending upon the receptor agonist applied with some agonists inducing greater $Ca^{2+}$ responses in DS than DR cells (Table 2). Among the three MCF-7 wt cell lines, the magnitude of the peak $[Ca^{2+}]_1$ induced by any given agonist was similar; thus, unless otherwise indicated, data relative to MCF-7 wt cells are representative of all three MCF-7 wt cell lines. Regardless of the agonist used, the onset kinetics of the receptor-evoked $[Ca^{2+}]_1$ rise were comparable among all the cell lines and rather fast [the overall onset $t_{1/2}$ (time needed to reach 50% of the $[Ca^{2+}]_1$ peak) was~10 sec., FIGS. 1-2].

EXAMPLE 4

DECAY KINETICS OF RECEPTOR-STIMULATED $[Ca^{2+}]_i$ INCREASE IN BREAST CANCER CELLS

The rapid onset phase of the receptor-mediated $Ca^{2+}$ response is followed by a slower decay phase during which the agonist-elevated $[Ca^{2+}]_1$ gradually declines towards basal levels. The decay kinetics of $[Ca^{2+}]_1$ increased by ATP, UTP, BK, or THR were found to markedly differ between wt, DS (MCF-7 as well as MDA-MB-23 1) cells and DR cells (FIGS. 1-2). To compare the decay kinetics among the various clones, the $[Ca^{2+}]_i$ decay $t_{1/2}$ (defined as: the time, sec., that the agonist-increased $[Ca^{2+}]_1$ takes to decline to 50% of the peak value while returning to resting levels, and calculated as: time at which 50% peak $[Ca^{2+}]_i$ is reached during decay phase minus time of peak $[Ca^{2+}]_1$ response) was used. The major finding of this study which constitutes the basis for this application is that MCF-7 derived DR clones exhibited a decay $t_{1/2}$ significantly longer than MCF-7 wt, DS cells (FIG. 3) with MCF-7/ADR and MCF-7/Ad-Vp cells showing the longest decay $t_{1/2}$ when compared to their respective parental cells. The estrogen receptor-negative MDA-MB-231 cells were used as another example of wt, DS breast cancer cell line and were found to exhibit basal $[Ca^{2+}]_1$ and receptor-mediated responses very similar, in magnitude and kinetics, to MCF-7 wt cells (Table 1-2; FIG. 2).

ATP induced a peak $[Ca^{2+}]_1$ increase of comparable (or slightly lesser) magnitude in standard buffer ($CaCl_2$: 0.3 mM) and buffer containing the $Ca^{2+}$ chelator, EGTA (4 mM), indicating that the primary cause for $[Ca^{2+}]_1$ increase is $Ca^{2+}$ mobilization from internal stores rather than $Ca^{2+}$ influx (FIG. 4 and Table 3). Because no capacitative $Ca^{2+}$ entry occurs in the absence of $Ca^{2+}_e$, (Berridge Nature 361:315-325, 1993), the decay kinetics are expected to be faster than in the presence of $Ca^{2+}_e$. The ATP-increased $[Ca^{2+}]_1$ decay of both DS and DR cells was indeed faster in the presence of EGTA, but always longer in DR cells than DS cells (Table 3). Interestingly, the absence of $Ca^{2+}_e$ affected the decay rate of DS and DR to a different extent. In MCF-7/ADR and MCF-7/C4 cells, decay kinetics were $\geq$60% faster in the absence than in the presence of $Ca^{2+}_e$, whereas in MCF-7 and MDA-MB-231 wt cells, decay kinetics were $\leq$40% faster in $Ca^{2+}$-free conditions (Table 3).

EXAMPLE 5

TG-EVOKED $[Ca^{2+}]_1$ INCREASE

All clones responded to TG, when applied as the first drug, with a comparable~3 fold increase in $[Ca^{2+}]_i$ (Table 2). As expected from the mode of action of TG the onset kinetics of the $Ca^{2+}$ response were slower than those of receptor-mediated but similar in DS and DR clones (onset $t_{1/2}$ for TG-induced peak $[Ca^{2+}]_1$ was~40 sec., FIG. 5). Also, in any given cell line, $[Ca^{2+}]_i$ increased by TG was slower in returning to basal level than the $[Ca^{2+}]_1$ increased by receptor agonists (FIG. 5). Because calcium up-take into the store is inhibited by TG, the efflux of the ion from the cells is now the major mechanism used by the cells to re-establish homeostatic calcium levels. Statistically significant differences in the decay kinetics of TG-increased $[Ca^{2+}]_1$ were detected between DS and the MCF-7/Ad-Vp and MCF-7/VP clones that exhibited a decay significantly longer than their DS counterpart (decay $t_{1/2}$ of the TG-induced $[Ca^{2+}]_1$ rise: MCF-7 wt-NIH=222.6±66.5 sec., n=19; MCF-7/Ad-Vp=662.2±147.3 sec., n=11, P<0.01, t-test; MCF-7 wt ATCC=173.1±30.5 sec., n=11; MCF-7/VP=330.7±48.5 sec., n=6, P<0.05, t-test). Following TG, ATP failed to evoke $Ca^{2+}$ responses in MCF-7 wt and MCF-7/ADR cells (FIG. 5) while inducing a modest and transient $[Ca^{2+}]_1$ increase in MCF-7/C4 (FIG. 5), MCF-7/VP and MCF-7/Ad-Vp cells (data not shown). With the exception of MCF-7 wt and MCF-7/VP cells, TG was able to increase $[Ca^{2+}]_1$ when applied after ATP in all DR clones as well as MDA-MB-231 wt cells (FIGS. 1 and 2).

EXAMPLE 6

EFFECTS OF P-GP AND MRP MODULATORS ON AGONIST-INDUCED $Ca^{2+}$ RESPONSES

Two DR clones subjected to this study express classic multi-drug resistance drug efflux pumps: MCF-7/ADR cells (showing the slowest $[Ca^{2+}]_1$ decay kinetics) express P-gp and MCF-7/VP cells (whose $[Ca^{2+}]_1$ decay was only~30% slower than DS cells) express MRP. We tested some of the most commonly used P-pg (VER and CSA) and MRP (GEN and PRO) modulators for their ability to affect the ATP-increased $[Ca^{2+}]_1$ decay of MCF-7/ADR and MCF-7/VP cells, respectively, and their DS counterpart. An acute (10 min) pre-treatment of the cells with VER (25 uM), CSA (10 uM), GEN (100 uM), PRO (2 mM) or the vehicle (0.1% DMSO for GEN and CSA; water for VER; 0.5N NaOH-pH equilibrated with 20 mM Na-HEPES for PRO) did not affect ATP-induced $[Ca^{2+}]_i$ responses with DR clones showing again slower decay kinetics than DS cells. DR and DS cells were then exposed to the modulators for 2 or 24 hr and challenged with ATP. As mentioned earlier, VER and CSA treatments greatly improved the loading of fura-2 in MCF-7/ADR cells. In general, basal $[Ca^{2+}]_1$ of MCF-7 wt, MCF-/VP and MCF-7/ADR cells was found not to be significantly affected by any of the drugs at either time point with the exception of a 2 hr treatment with VER which significantly reduced MCF-7/ADR cell resting $[Ca^{2+}]_1$ compared to vehicle-treated cells (basal $[Ca^{2+}]_1$ in nM: vehicle-treated = 69±13, n=14; VER-treated=28±7, n=12; P<0.05, t-test). FIG. 6 shows that the decay kinetics of wt or MCF-7/ADR and MCF-7/VP cells were not affected by VER/CSA or GEN/PRO, respectively, with no decay $t_{1/2}$ values being lower than those of vehicle-treated cells (dotted line in FIG. 6). Indeed, the decay $t_{1/2}$ of ATP-evoked $Ca^{2+}$ response in MCF-7/ADR cells remained significantly greater than wt, DS cells, even after a 24 hr exposure to the drugs [VER: MCF-7/ADR=132±20 sec., n=9; MCF-7 wt=46±6.3 sec., n=9; P=0.008, t-test; CSA: MCF-7/ADR=317±45 sec., n=8; MCF-7 wt=58.3±10 sec., n=13; P<0.001, t-test]. Likewise, the decay $t_{1/2}$ ATP-evoked $Ca^{2+}$ response in MCF-7/VP cells treated for 24 hr with GEN or PRO remained longer than wt, DS cells [GEN. MCF-7/VP=64.3±10.5 sec., n=12; MCF-7 wt=42.1±6.3 sec., n=9; PRO: MCF-7/VP=58.3±7.1 sec., n=12; MCF-7 wt=43.2±4.5 sec., n=9].

EXAMPLE 7

COMPARISON OF THE $[Ca^{2+}]_1$ RESPONSE AND DECAY EVOKED BY BK IN C6 WILD TYPE AND DR CLONAL CELLS

C6 cell lines, plated on the same day, were loaded with Fura-2 and imaged on the same day. BK(10uM), ATP (50uM), and/or TG (1 uM) were added to the cells after resting $[Ca^{2+}]_1$ was recorded for 30-60 sec. Peak $[Ca^{2+}]_1$ increase and decay $t_{1/2}$ were calculated from each coverslip (up to 99 cells simultaneously imaged) per each cell lines. In each experiment, peak $[Ca^{2+}]_1$ increase and decay $t_{1/2}$ values from each DR clone were compared to those from wild type C6 cells and expressed in percent of wild type response. While the fold increase in $[Ca^{2+}]_1$ evoked by BK progressively decreases from clone A to clone E, the decay $t_{1/2}$ becomes greater with clone E (showing the highest degree of resistance to adriamycin) also being the one with the slowest decay kinetics compared to wild type cells.

Various modifications and variations of the described methods and products and the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical, biological, pharmacological or chemical arts or related fields are intended to be within the scope of the following claims.

The invention claimed is:

1. A method for determining the resistance of a cell to a drug comprising:
   (a) determining an intracellular decay time for calcium ions in one or more test cell(s) and one or more control cell(s) after exposure to an ion elevating agent, wherein the test cell(s) is a breast cancer cell or a glioblastoma cell,
   (b) comparing the intracellular decay time for calcium ions in the test cell(s) with the intracellular decay time for calcium ions in the control cell(s), and
   (c) correlating a difference between the intracellular decay time for calcium ions in the test cell(s) and the intracellular decay time for calcium ions in the control cell(s) to determine the resistance to the drug of the one or more test cell(s).

2. The method of claim 1 wherein said step of correlating includes correlating a greater intracellular decay time of said calcium ions in said one or more test cell(s) than intracellular decay time of said calcium ions in said one or more control cell(s) with said resistance to said drug.

3. The method of claim 2 wherein said drug is a chemotherapeutic drug for treating cancer.

4. The method of claim 3 wherein said chemotherapeutic drug is selected from the group consisting of a DNA intercalating agent, a DNA topoisomerase I inhibitor, a DNA topoisomerase II inhibitor, and a DNA alkylating agent.

5. The method of claim 2 wherein said ion elevating agent is an agonist of calcium mobilization.

6. The method of claim 5 wherein said agonist of calcium mobilization is one or more of ATP, UTP, BK, THR, and TG.

7. The method of claim 2 wherein said test cell(s), control cell(s), or both, is a breast cancer cell.

8. The method of claim 2 wherein said test cell(s), control cell(s), or both, is a glioblastoma cell.

9. The method of claim 2 wherein said test cell(s) are obtained from a cell culture.

10. The method of claim 2 wherein said test cell(s) are obtained from a biopsy.

11. The method of claim 2 wherein said control cell(s) are obtained from a cell culture.

12. The method of claim 2 wherein said control cell(s) are obtained from a biopsy.

13. The method of claim 2, wherein said intracellular decay times of said test cell(s) and said control cell(s) are determined by single cell fluorescence digital imaging.

14. The method of claim 1 wherein said step of correlating includes correlating a lesser intracellular decay time of said calcium ions in said one or more test cell(s) than said intracellular decay time of said calcium ions in said one or more control cell(s) with said sensitivity to said drug.

15. The method of claim 14 wherein said drug is a chemotherapeutic drug for treating cancer.

16. The method of claim 15 wherein said chemotherapeutic drug is selected from the group consisting of a DNA intercalating agent, a DNA topoisomerase I inhibitor, a DNA topoisomerase II inhibitor, and a DNA alkylating agent.

17. The method of claim 14 wherein said ion elevating agent is an agonist of calcium mobilization.

18. The method of claim 17 wherein said agonist of calcium mobilization is one or more of ATP, UTP, BK, THR, and TG.

19. The method of claim 14 wherein said test cell(s), control cell(s), or both, is a breast cancer cell.

20. The method of claim 14 wherein said test cell(s), control cell(s), or both, is a glioblastoma cell.

21. The method of claim 14 wherein said test cell(s) are obtained from a cell culture.

22. The method of claim 14 wherein said test cell(s) are obtained from a biopsy.

23. The method of claim 14 wherein said control cell(s) are obtained from a cell culture.

24. The method of claim 14 wherein said control cell(s) are obtained from a biopsy.

25. The method of claim 14, wherein said intracellular decay times of said test cell(s) and said control cell(s) are determined by single cell fluorescence digital imaging.

* * * * *